(12) United States Patent
Sayger

(10) Patent No.: US 12,408,965 B2
(45) Date of Patent: Sep. 9, 2025

(54) BONE SLIVER REMOVAL SYSTEM

(71) Applicant: Crossroads Extremity Systems, LLC, Memphis, TN (US)

(72) Inventor: Daniel Sayger, Olive Branch, MS (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 474 days.

(21) Appl. No.: 18/058,889

(22) Filed: Nov. 28, 2022

(65) Prior Publication Data

US 2023/0165616 A1 Jun. 1, 2023

Related U.S. Application Data

(60) Provisional application No. 63/264,776, filed on Dec. 1, 2021.

(51) Int. Cl.
*A61B 17/88* (2006.01)
*A61B 17/15* (2006.01)
*A61B 17/56* (2006.01)

(52) U.S. Cl.
CPC ........ *A61B 17/8897* (2013.01); *A61B 17/152* (2013.01); *A61B 2017/565* (2013.01)

(58) Field of Classification Search
CPC .......................... A61B 17/8897; A61B 17/152
See application file for complete search history.

(56) References Cited

U.S. PATENT DOCUMENTS

| 11,058,546 | B2* | 7/2021 | Hollis | .................... | A61F 2/4225 |
| 2004/0138662 | A1* | 7/2004 | Landry | ................ | A61B 17/861 606/279 |
| 2005/0143745 | A1* | 6/2005 | Hodorek | ............ | A61B 17/1764 606/87 |
| 2008/0086114 | A1* | 4/2008 | Schmitz | ................ | A61M 25/09 606/1 |
| 2021/0251670 | A1* | 8/2021 | Sayger | ............... | A61B 17/1775 |

* cited by examiner

*Primary Examiner* — Christian A Sevilla
(74) *Attorney, Agent, or Firm* — BakerHostetler

(57) ABSTRACT

A surgical tool and related methods are provided for removal of a bone sliver from a resected joint. The tool can include a housing including an upper end, a lower end, and a channel extending from the upper end to the lower end. A paddle member extends from the lower end of the housing. The paddle member includes a paddle shaft and a paddle head. The surgical tool further includes an insertion member that has a handle end, an extension that extends from the handle end, and a cutting tip. The extension is translatable within the channel such that the handle end and the cutting tip can move relative to the housing between a retracted position and an advanced position.

20 Claims, 18 Drawing Sheets

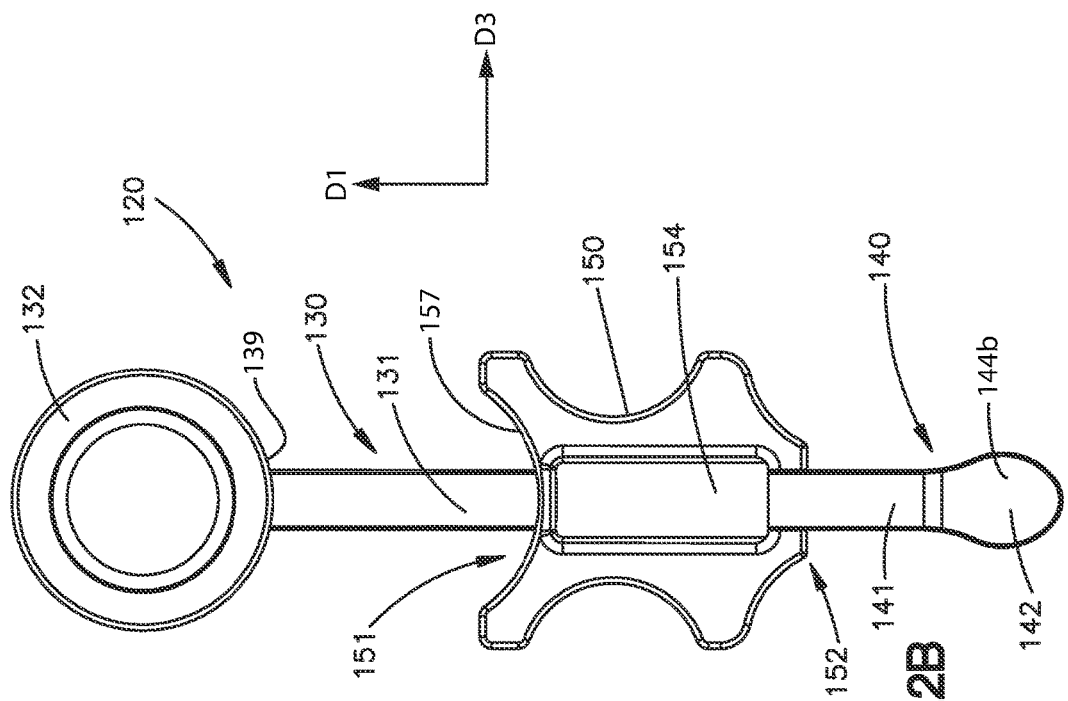
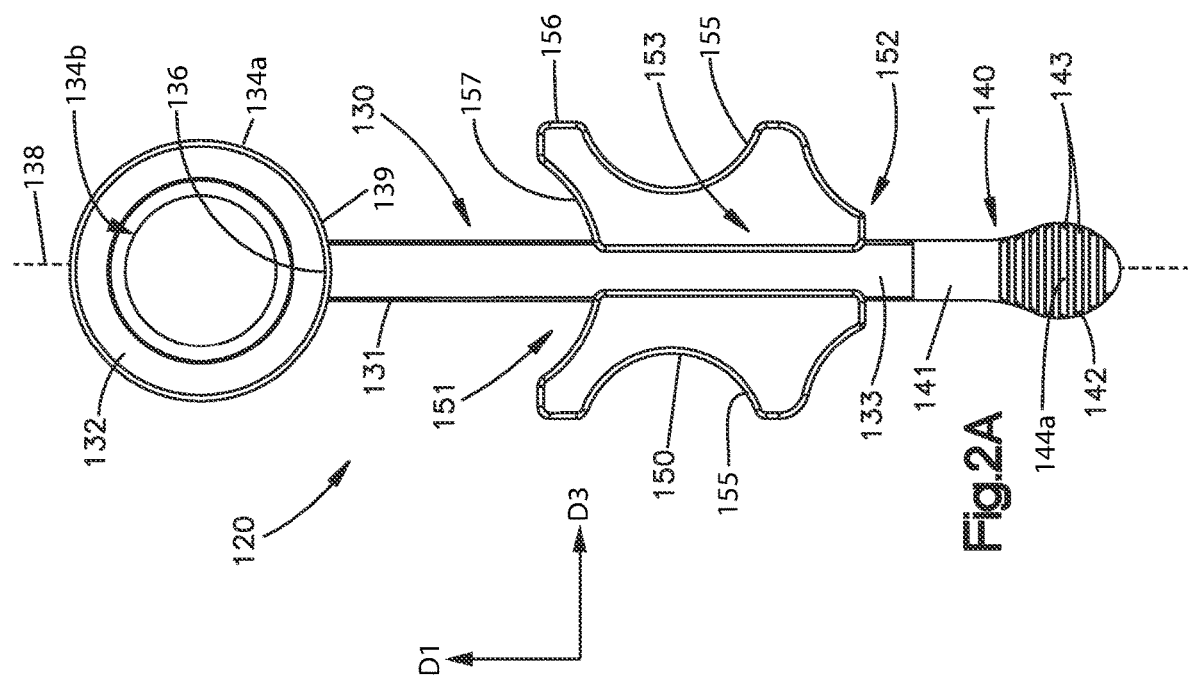

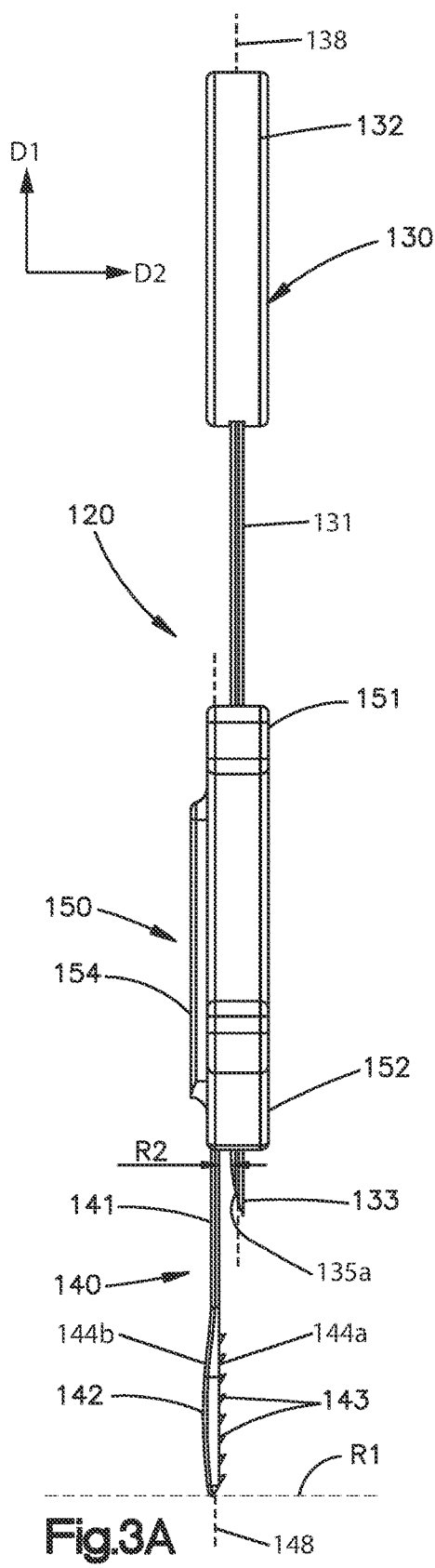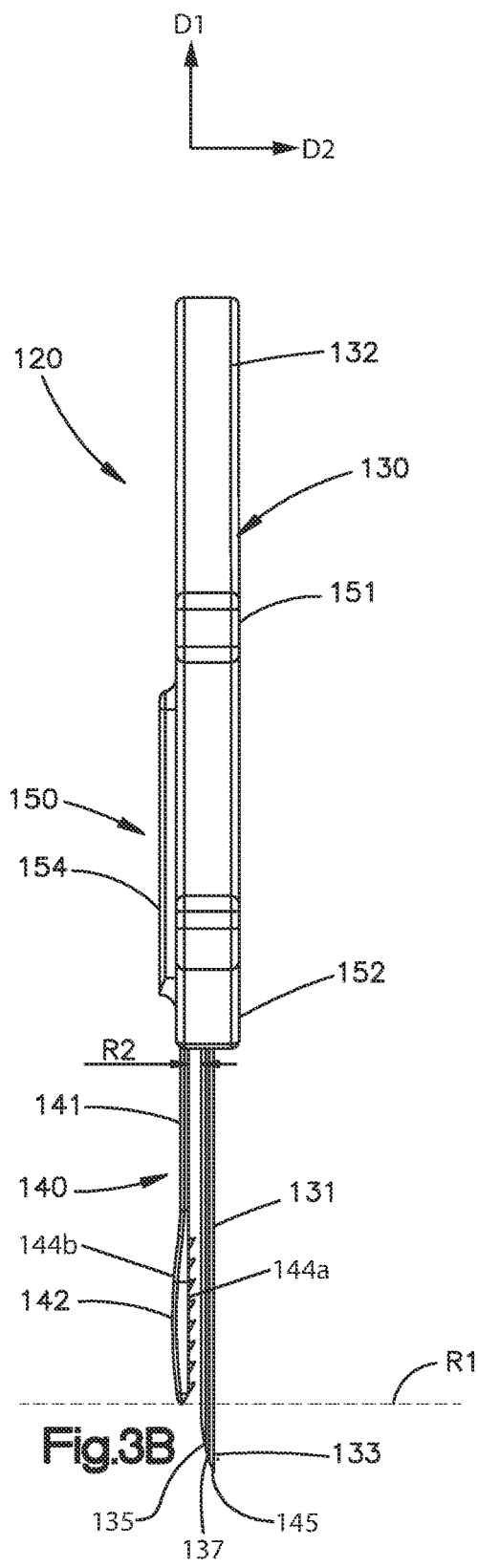

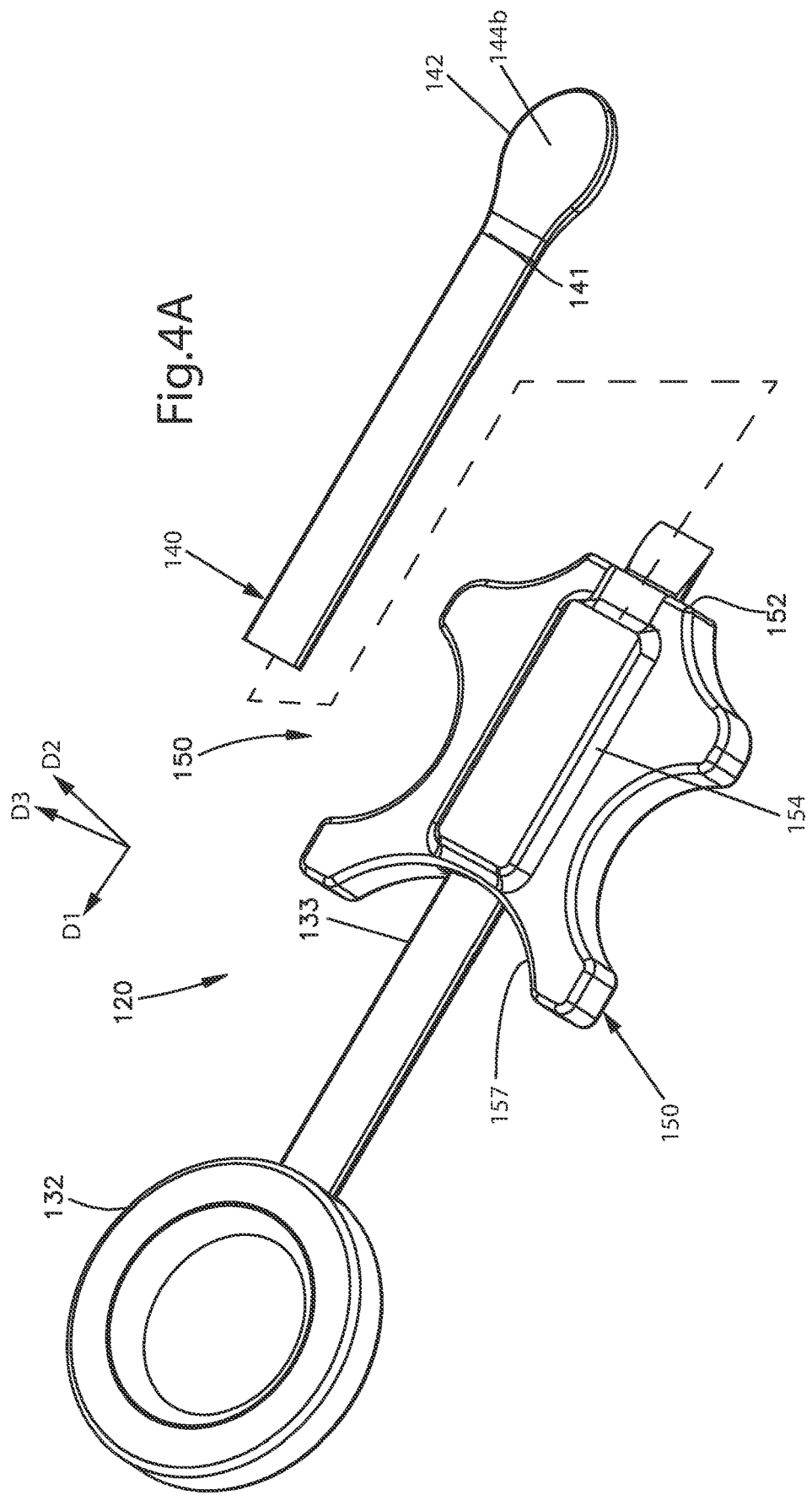

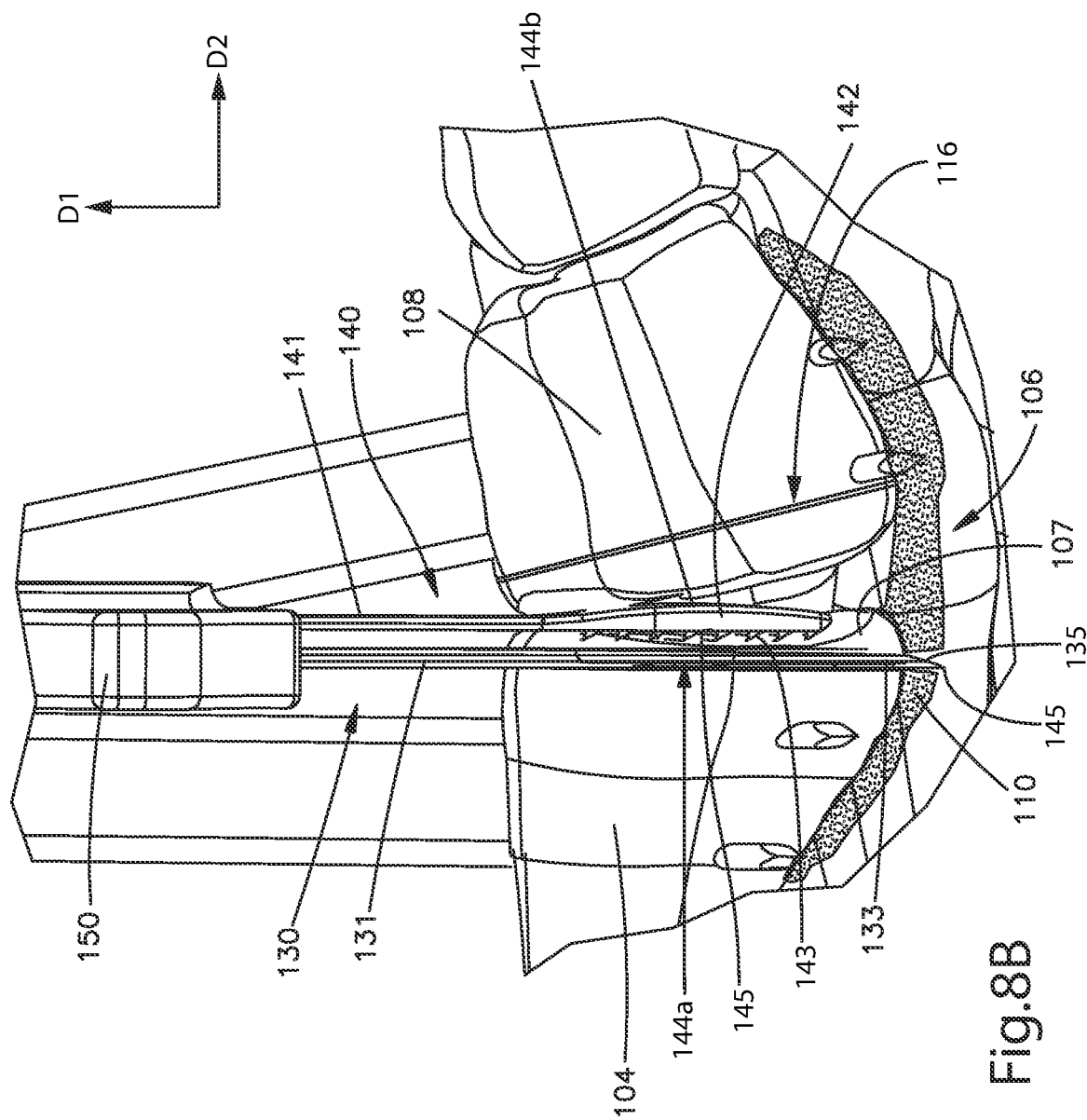

BONE SLIVER REMOVAL SYSTEM

CROSS REFERENCE TO RELATED APPLICATIONS

This claims priority to U.S. Patent Application Ser. No. 63/264,776 filed Dec. 1, 2021, the disclosure of which is hereby incorporated by references as if set forth in its entirety herein.

BACKGROUND

Field

This disclosure generally relates to surgical systems for resecting joints and particularly to procedures for correcting a bunion in a patient's foot.

Related Art

A bunion is a deformity of the foot characterized by misalignment between the first metatarsal and the proximal phalanx of a patient's great toe. Bunions can be painful and make walking difficult. Surgical methods for correcting bunions can include resection of the tarsometatarsal joint to provide clearance for repositioning and alignment of the metatarsal bone. The resection can create anatomical material that can be difficult to remove from the joint. What is therefore needed is a method and apparatus for removing anatomical material from a joint space.

SUMMARY

A first aspect of the disclosure is a method of correcting alignment between a metatarsal and a cuneiform bone by fusing a tarsometatarsal (TMT) joint between an end of the metatarsal and the cuneiform bone. A first wire is inserted into the metatarsal, inserting a second wire into the metatarsal. A first guide aperture of a cut guide is inserted over the first wire and a second guide aperture of the cut guide is inserted over the second wire to align a slot of the cut guide with the end of the metatarsal. The end of the metatarsal is resected through the slot to form a resected face and separated bone material along a cut line. A paddle member of a bone material removal tool is inserted into the TMT joint between the separated bone material and the cuneiform bone. An insertion member of the bone material removal tool is advanced into the TMT joint between the resected face and the separated bone material with the separated bone material between the insertion member and the paddle member. Advancing the insertion member includes extending a tip of the insertion member past the paddle member and severing a plantar tarsometatarsal ligament of the TMT joint and pinching the separated bone material between the insertion member and the paddle member. The separated bone material is removed from the TMT joint using the bone material removal tool. A third wire and a fourth wire are inserted into the cuneiform bone A position of the metatarsal and cuneiform bones is moved into a corrected configuration and fixed in the corrected configuration.

A second aspect of the disclosure is a method of correcting alignment between a first bone and a second bone by fusing a joint therebetween. A paddle member of a bone material removal tool is inserted into the joint between the separated bone material and the second bone. An insertion member of the bone material removal tool is advanced relative to the paddle member and into the joint between the resected face and the separated bone material. The separated bone material is removed from the joint with the separated bone material between the insertion member and the paddle member.

According to another aspect, a first wire is inserted into the first bone. A second wire is inserted into the first bone. A first guide aperture of cut guide is inserted over the first wire and a second guide aperture of the cut guide is inserted over the second wire to align a slot of the cut guide with the end of the first bone. The end of the first bone is resected through the slot. According to another aspect, a third wire and a fourth wire are inserted into the second bone. A positioning of the first and second bones is moved into a corrected configuration. The first and second bones are fixed in the corrected configuration. According to another aspect, the insertion member includes a cutting tip and advancing the insertion member includes extending the cutting tip past the paddle member and severing at least one ligament of the joint. According to another aspect, the at least one ligament includes a plantar tarsometatarsal ligament and the joint is a TMT joint. According to another aspect, advancing the insertion member along the resected face and the separated bone material flexes the paddle member to create a compression force on the separated bone material between the insertion member and the paddle member. According to another aspect, the paddle member includes a plurality of retention barbs.

A third aspect of the disclosure includes a surgical tool for removal of a resected bone material. The tool includes a housing with an upper end, a lower end, and a channel extending from the upper end to the lower end. A paddle member extends from the lower end of the housing, the paddle member including a shaft and a head. An insertion member includes a handle end, an extension and a tip portion. The extension slidably mounts within the channel such that the handle end and the tip portion can move relative to the housing along a first dimension between an advanced configuration and a retracted configuration.

According to another aspect, the head of the paddle member includes a plurality of retention features, the retention features on a first side of the head facing the insertion member.

According to another aspect, the plurality of retention features include angled horizontal slots. According to another aspect, the plurality of retention features include barbs.

According to another aspect, the upper end of the housing includes a concave portion configured to receives a convex portion of the handle end of the insertion member in the advanced configuration. According to another aspect, the convex portion of the handle end of the insertion member includes a ring. According to another aspect, the extension of the insertion member is parallel with the shaft of the paddle member. According to another aspect, the insertion member includes a cutting tip and, in the advanced configuration, the cutting tip extends past the head of the paddle member in the first dimension. According to another aspect, in the advanced configuration, the insertion member is laterally offset from the paddle member by an offset distance. According to another aspect, the shaft of the paddle member is more flexible than the extension of the insertion member and is configured to flex outwardly when the insertion member is extended from the retracted configuration to the advanced configuration with bone material having a thickness greater than the offset distance positioned between the paddle member and the insertion member and to provide a retention force against the bone material and the insertion member.

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein.

BRIEF DESCRIPTION OF THE DRAWINGS

Various examples are depicted in the accompanying drawings for illustrative purposes, and should in no way be interpreted as limiting the scope of the examples. Various features of different disclosed examples can be combined to form additional examples, which are part of this disclosure.

FIG. 2A is a front elevation view of a bone removal tool.

FIG. 2B is a rear elevation view of the bone removal tool.

FIG. 3A is a side elevation view of the bone removal tool shown in a retracted configuration whereby an insertion member of the bone removal tool in a retracted position;

FIG. 3B is a side elevation view of the bone removal tool in an advanced configuration whereby the insertion member in an advanced position;

FIG. 4A is an exploded perspective view of the bone removal tool shown with the insertion member in the advanced configuration;

FIG. 8B is an enlarged side elevation view of the patient's foot showing the TMT joint of FIG. 8A;

DETAILED DESCRIPTION

The various features and advantages of the systems, devices, and methods of the technology described herein will become more fully apparent from the following description of the examples illustrated in the figures. These examples are intended to illustrate the principles of this disclosure, and this disclosure should not be limited to merely the illustrated examples. The features of the illustrated examples can be modified, combined, removed, and/or substituted as will be apparent to those of ordinary skill in the art upon consideration of the principles disclosed herein.

The present disclosure can be understood more readily by reference to the following detailed description taken in connection with the accompanying figures and examples, which form a part of this disclosure. It is to be understood that this disclosure is not limited to the specific devices, methods, applications, conditions, or parameters described and/or shown herein, and that the terminology used herein is for the purpose of describing particular embodiments by way of example only and is not intended to be limiting of the scope of the present disclosure.

Figure 1:
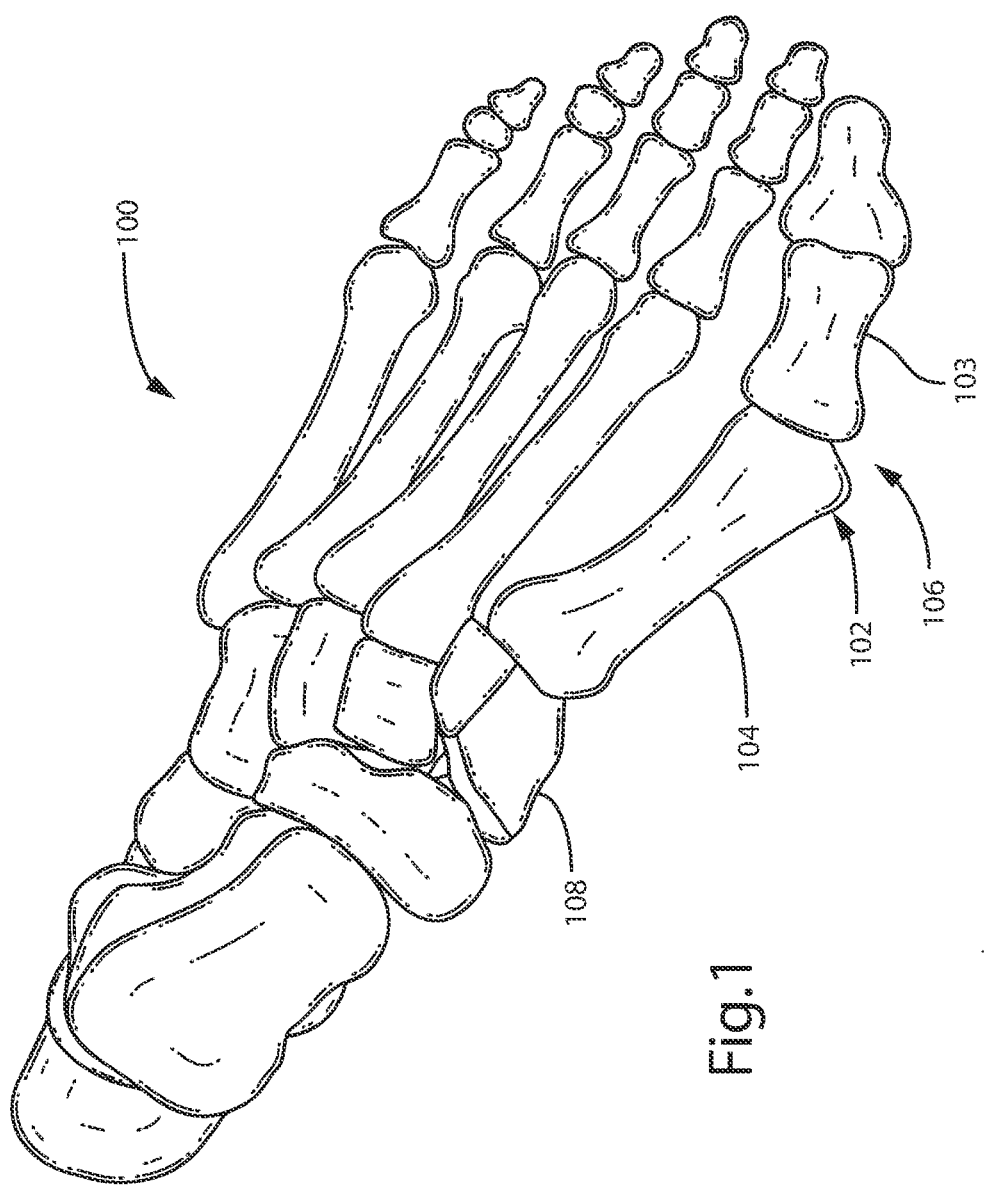
FIG. 1 is a perspective view of a patient's foot in a deformed configuration.
Figure 4B:
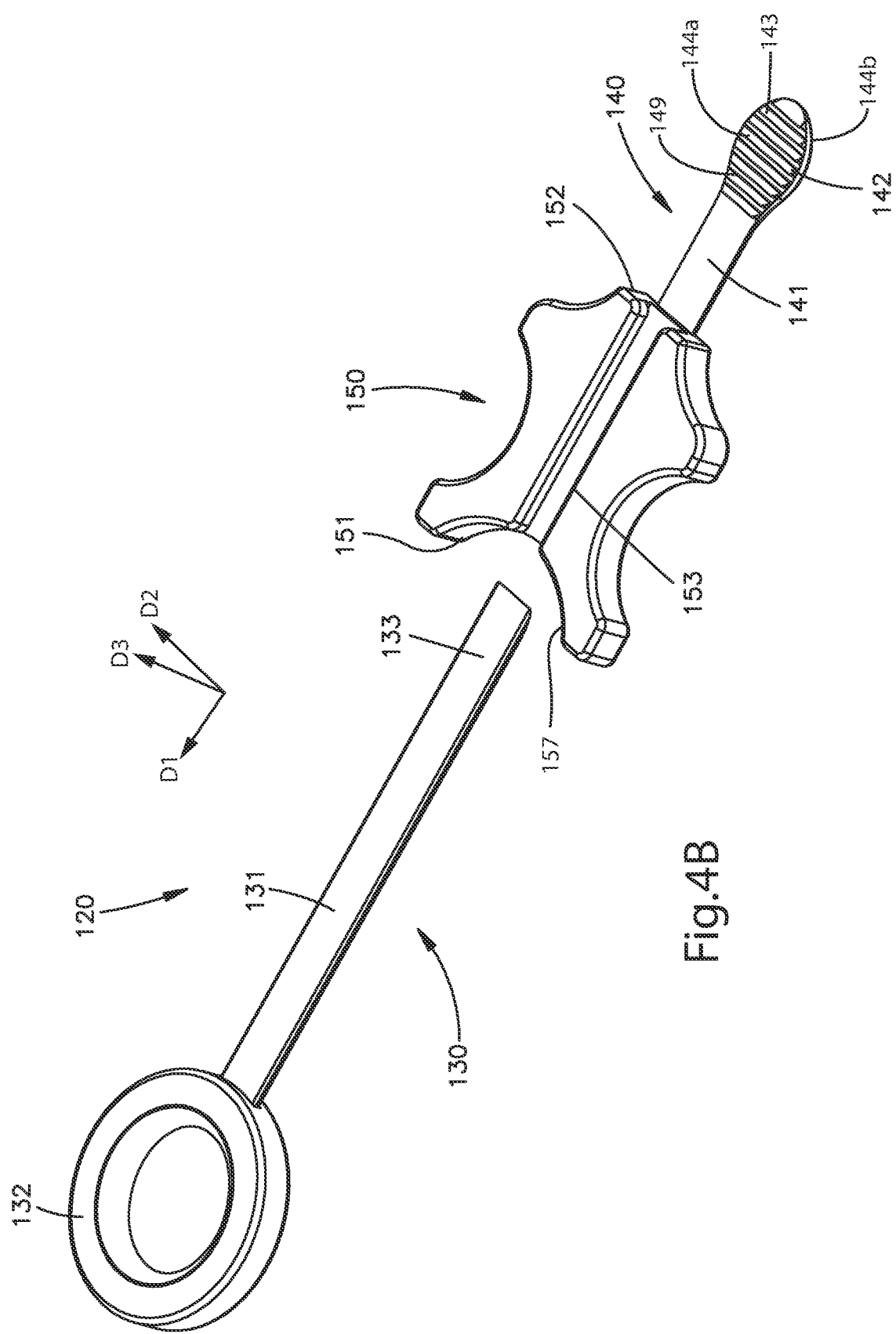
FIG. 4B is an exploded perspective view of the bone removal tool.

Referring to FIG. 1 shows, a skeletal view of a patient's foot 100 is shown having one or more bones such as a medial cuneiform bone 108, a first metatarsal 104, and a proximal phalanx 103 of the patient's great toe. The foot 100 defines a tarsometatarsal joint or TMT joint 106 between the metatarsal 104 and the medial cuneiform bone 108. The foot 100 is shown in an initial or deformed configuration having a deformity such as a bunion 102. The metatarsal 104 can be misaligned with the phalanx 103 when the foot 100 is in the deformed configuration. The metatarsal 104 can be oriented at an angle with respect to the phalanx 103. A high degree of misalignment between the metatarsal 104 and the proximal phalanx 103 can lead to severe pain and rubbing and discomfort and other problems in the patient's foot 100. Accordingly, it can be beneficial to correct the alignment between the metatarsal 104 and the proximal phalanx 103 of the great toe.

A proximal end of the first metatarsal 104 can be connected with a distal end of medial cuneiform bone 108, for instance by one or more ligaments. A proximal direction is defined from the metatarsal 104 toward the medial cuneiform bone 108. Conversely, a distal direction is defined from the medial cuneiform bone 108 toward the metatarsal 104. FIGS. 1-11 illustrate systems and methods of correcting alignment between the metatarsal 104 and the medial cuneiform bone 108. In turn, proper alignment between the metatarsal 104 and the medial cuneiform bone 108 can correct alignment between the metatarsal 104 and the proximal phalanx 103. Accordingly, the bunion 102 of the patient's foot 100 can be corrected. The present disclosure relates to systems and methods for correcting the deformed configuration. Moreover, the systems and methods described herein can be used more generally for correcting alignment between any two bones a patient's body.

As will now be described with reference to FIGS. 2-4, embodiments described herein include methods and tools, such as a bone removal tool 120, for removing bone material. In particular, embodiments described herein include tools and methods for removing bone material from a joint. In one example, embodiments described herein include tools and methods for removing bone material from the TMT joint 106 (see FIG. 1). The bone material can be defined by a sliver of bone formed after resection from a bone. In one example, the sliver of bone can be defined by the metatarsal bone. In another example, the sliver of bone can be defined by the cuneiform bone. While tools and methods described herein can have particular applicability to the TMT joint during correction of a bunion 102, it should be appreciated that the tools and methods described herein can apply to any suitable bone sliver created during any suitable surgical procedure as desired.

As shown at FIGS. 2A-4 a deformity correction system can include a bone removal tool 120 that is configured to remove bone material from a joint, such as the TMT joint. The bone removal tool 120 can facilitate joint resection surgeries by removing bone fragments and/or cutting soft or hard tissues within the joint. The bone removal tool 120 can be particularly helpful for removing portions of bone, or bone slivers, that are cut from other portions of bone during a resection of joint. The bone removal tool 120 can also function to cut one or more remaining ligaments that may be attached to the sliver and prevent the sliver from being easily removed from within a joint after the bone is resected.

The bone removal tool 120 can include a first member such as an insertion member 130, and a complementary second member such as a paddle member 140 that are configured to cooperate with each other so as to couple the bone removal tool 120 to a bone sliver. The insertion member 130 can be configured as an osteotome or other suitable cutting instrument. The insertion member 130 can be sharpened so as to fit between a bone sliver that has been resected from a bone and a remaining portion of the bone that remains after the bone sliver has been resected. The insertion member 130 can further be configured to sever one or more soft tissue attachments of the TMT joint The insertion member 130 can include a handle 132, and an extension 131 that extends from the handle 132 along a central axis 138 and terminates at a tip portion 133. The extension 131 can be a linear member having a rectangular cross-sectional profile or any suitable alternative shape as desired. The handle 132 can be attached to a first end 136 of the extension 131 or can be monolithic with the first end of the extension 131 as desired. The handle 132 can define an outer perimeter 134a that defines an opening 134b in some examples. The handle portion 132 can thus facilitate a user to grasp and hold onto the insertion member 130. In some examples, the perimeter 134a of the handle 132 can define a circular or otherwise round ring. The tip portion 133 can terminate at a tip which can be sharpened so as to define a blade 135. The blade 135 can be disposed in an opposition to the first end 136 of the extension 131. The blade 135 can be defined be at least one bevel 137, such as a single bevel 137, that tapers to a cutting tip 145 as it extends in a direction defined from the first end 136 to the tip portion 133. The tip 145 can be a sharp cutting tip in some examples. The bevel 137 can be positioned to face the paddle member 140 in some examples. Further, the tip portion 133 can define a single blade 135 or multiple blades as desired. Further, the blade 135 can be substantially straight, or can include serrations as desired, for instance. Thus, the blade 135 can be configured to cut remaining bone that may remain attached after the resection is performed, or soft tissue such as a ligament as desired.

The bone removal tool 120 can further include a housing 150 that is configured to slidingly receive the extension 131. Further, the housing 150 can define a central member of the surgical tool 120 and act as a grip of the bone removal tool 120. Thus, a user can grip the bone removal tool 120 by putting a thumb through the opening 134b, and placing fingers into respective recesses 155 defined by the outer surface 156 of the housing 150. The housing 150 can include an upper end 151 and a lower end 152 that opposite the upper end 151 along a downward direction. During operation, the downward direction can define an insertion direction into the joint 106 (see FIG. 1). Conversely, the upper end 151 is opposite the lower end 152 along an upward direction, which can also be referred to as a removal direction opposite the insertion direction. Thus, the bone removal tool 120 can define a first direction D1 that includes the upward direction and the downward direction. It is appreciated that the housing 150 defines the upper end 151 and the lower end 152 regardless of the orientation of the housing 150 during use. For instance, it is envisioned that during use the housing 150 can be oriented such that the upper end 151 is not, in fact, spatially positioned above the lower end 152. Nevertheless, the upper end 151 and the lower end 152 are defined in such orientations. The upper end 151 can define a concave surface 157 that is sized and configured to receive a portion of the handle 132.

The bone removal tool 120 can further define a channel 153 that extends between the upper end 151 and the lower end 152. For instance, the channel 153 can extend from the upper end 151 to the lower end 152. The channel 153 can extend from the upper end 151 to the lower end 152. The channel 153 can be fully closed or partially open. The channel 153 can include an inner cross sectional shape that is sized to fit the extension 131 of the insertion member 130. Thus, the extension 131 can be inserted into the channel 153 at the upper end 151 in the downward direction such that the blade 135 defines a leading end into the channel 153. The insertion member 130, and in particular the extension 131, can be removed from the housing, for instance to facilitate cleaning or replacement of component parts of the bone removal tool 120, including either or both of the housing 150 and the insertion member 130. In particular, the extension can be removed from the channel 153 by sliding the extension in the upward direction until the extension 131 travels entirely out of the channel 153 at the upper end 151. The channel 153 can capture the extension 131 to prevent removal of the extension 131 in a lateral direction perpendicular to the upward and downward directions.

The insertion member 130, and in particular the extension 131, can be slidable within the channel 153 between a retracted position as shown in FIGS. 2A-2B and 3A and an advanced position as shown in FIGS. 3B-4A. The bone removal tool 120 can be said to be in an advanced configuration when the extension 131 is in the advanced position. Conversely, the bone removal tool 120 can be said to be in a retracted configuration when the extension 131 is in the retracted position. When the extension 131 is in the advanced position, the blade 135 at an advanced position that is spaced in the downward direction with respect to a retracted position of the blade 135 when the extension 131 is in the retracted position. When the insertion member 130 is in the advanced position, the portion of the handle 132 can interface with the concavity defined by the concave surface 157 defined by the upper end 151 of the housing 150, such that the portion of the handle 132 is received in the concavity defined by the concave surface 157. In some examples, the portion of the handle 132 can define a convex surface 139. Thus, the surface 139 of the handle 132 can nest in the surface 157 of the housing 150. It should be appreciated, of course, that the surfaces 139 and 157 can define any suitable size and shape as desired. In some examples, the portion of the handle 132 can interface with the concavity defined by the concave surface 157 such that the portion of the handle 132 abuts the concave surface 157 when the insertion member 130 is in the advanced position. In this regard, the surfaces 139 and 157 can define respective abutment surfaces of the handle 132 and the housing 150. The interface between the handle 132 and the housing 150 can provide a feedback mechanism for the operator to indicate that the insertion member 130 has been fully extended to the advanced position.

With continuing reference to FIGS. 2A-4B, and as described above, the bone removal tool 120 can further include the paddle member 140. The paddle member 140 can include a paddle shaft 141 and a paddle head 142 that extends from the paddle shaft 141. The paddle shaft 141 extends out from the housing 150 along a central paddle axis 148 in the downward direction to the paddle head 142. In particular, the paddle shaft 141 can extend from a lower end 152 of the housing 150 in the downward direction. The central paddle axis 148 and the central axis 138 of the extension 131 can be oriented along the first direction D1. The paddle shaft 141 can be an elongate linear portion having a rectangular-shaped cross sectional profile or suitable alternative shape. In one example, the housing 150 can include a receptacle 154. The receptacle 154 can be located on an opposite side with respect to the side that defines an opening to the slot 153. The receptacle 154 can include an inner receiving space that receives an end portion of the paddle shaft 141 of the paddle member 140 that is opposite the paddle head 142. The paddle shaft 141 is inserted into the receptacle 154 in the upward direction until the paddle shaft 141 abuts the housing 150, at which point the paddle shaft 141 is fully seated in the receptacle 154. In some examples, the paddle member 140 can be removable from the receptacle 154. This can facilitate cleaning or replacement or component parts of the bone removal tool 120, including either or both of the housing 150 and the paddle member 140. It should be appreciated, of course, that the paddle shaft 141 can be attached to the housing 150 in any suitable alternative manner. Alternatively, the housing 150 and the paddle shaft 141 can be monolithic with each other.

The paddle head 142 can be disposed at a lower end of the paddle shaft 141. The paddle head 142 can be attached to the paddle shaft 141 in any suitable manner. Alternatively, the paddle head 142 can be monolithic with the paddle shaft 141. The paddle head 142 can define first and second major surfaces 144a and 144b that are opposite each other in a second direction D2 that is perpendicular to the first direction D1. The first major surface 144a can face the extension 131 when the extension 131 is in the advanced position. Thus, the extension 131 and the paddle head 142 can be aligned along the second direction D2 when the extension 131 is in the advanced position. The extension 131, and in particular the blade 135, can be offset with respect to the paddle head 142 in the upward direction when the extension is in the retracted position. Further, the first major surface 144a can be on the same side of the bone removal tool 120 as the opening to the channel 153.

The paddle head 142 can be an enlarged head having a width that is greater than a width of the shaft 141 in a third direction D3 that is perpendicular to each of the first direction D1 and the second direction D2. Each of the first and second major surfaces 144a and 144b can have respective outer perimeters that are generally curved, such as circular, or can define any suitable shape as desired. For instance, the head 142 can have substantially the same cross-sectional size and shape as the paddle shaft 141, such that the head 142 is as an extension of the paddle shaft 141. The head 142 can have a thickness from the first major surface 144a to the second major surface 144b along the second direction D2. The thickness can be flattened so as to be insertable into a joint between two bones, such as within the TMT joint 106 (see FIG. 1). In one example, either or both of the first and second major surfaces 144a and 144b can be substantially coplanar with the paddle shaft 141.

In some examples, the insertion member 130 can be oriented parallel with the paddle member 140. Specifically, the extension 131 can be oriented parallel with the shaft 141 of the paddle member 140. The extension 131 can be parallel with the shaft 141 in either or both of the retracted and advanced positions, and/or as the insertion member 130 moves between the retracted and advanced positions. The bone removal tool 120 can define an offset distance R2 in the second direction D2 from an inner face of the paddle shaft 141 to an inner face of the extension 131 that faces the inner face of the paddle shaft 141. In particular, the inner faces of the paddle shaft 141 and the extension 131 can face each other along the second direction D2. In certain examples, the offset distance R2 can be the same in both the retracted configuration and the advanced configuration. In certain implementations, the inner face of the paddle shaft 141 can be coplanar with the first major surface 144a of the paddle head 142, which can define an inner face of the head 142. Thus, the offset distance R2 can also be defined in the second direction D2 from the first major surface 144a of the paddle head 142 to the inner face of the extension 131. The second major surface 144b of the paddle head 142 can define an outer face of the head 142. The second major surface 144b can be shaped as desired. In one example, the second major surface 144b is convex in a plane that includes the first direction D1 and the second direction D2.

The paddle head 142 can comprise a plurality of the retention features 143. In particular, the retention features 143 can extend out from the first major surface 144a that is configured to face the insertion member 130, and in particular the extension 131, when the extension 131 is in the advanced position. The retention features 143 can be configured as a plurality of projections 149 that extend out from the first major surface 144a. The projections 149 can be angled as they extend out from the first major surface 144a. For instance, the projections 149 can be angled in the upward direction as they extend out from the first major surface 144a. Alternatively, the projections 149 can extend out from the first major surface 144a in a direction substantially orthogonal to the central paddle axis 148.

While the retention features 143 can be configured as projections such as barbs in one example, the retention features 143 can alternatively comprise one or more slots that extend into the first major surface 144a, alternatively configured projections, a roughened or textured surface, or other features that can assist in retaining the paddle member 140, and specifically the paddle head 142, within a joint. For instance, it is recognized that the paddle head 142 can be advanced in the downward direction of insertion as it is inserted into a joint. Thus, the retention features 143 can be angled in a direction opposite the direction of insertion as they extend away from the first major surface 144a. Thus, the retention features 143 can facilitate advancement of the head 142 into the joint. Once the paddle head 142 is disposed in the joint, it can be removed from the joint by moving the paddle head 142 in an upward removal direction. Because the retention features 143 can be angled in a removal direction as they extend away from the first major surface 144a, the retention features 143 can resist removal of the paddle head 142 from the joint.

During operation, and referring to FIG. 3A, the bone removal tool 120 can be in an initial retracted configuration whereby the tip portion 133 of the insertion member 130 is retracted within the housing 150 or disposed between the housing 150 and the paddle head 142 with respect to the first direction D1. Thus, the tip portion 133 can be said to be retracted relative to the paddle head 142. Thus, the tip portion 133 can be retracted within the channel 153 or adjacent to the channel 153. Accordingly, a reference line R1 that extends along a direction perpendicular to the first direction, such as the second direction D2, along a downward-most end of the paddle head 142 does not pass through the extension 131 when the insertion member 130 is in the retracted position. In particular, the extension 131 is spaced from the reference line R1 in the upward direction.

As shown in FIG. 3B, The bone removal tool 120 can be moved from the retracted configuration to the advanced configuration. In particular, the extension 131 can be advanced in the downward direction in the channel 153 of the housing 150 relative to the housing 150 and the paddle 140 from the retracted position to the advanced position. The insertion member 130 can be advanced to the advanced position manually. For instance, the user's thumb can apply a downward advancement or insertion force to the handle 132 while fingers of the user engage the housing 150 to provide a counterforce that stabilizes the housing 150 with respect to the handle 132. Therefore, the force applied to the handle 132 in the downward direction causes the insertion member 130 to move in the downward direction relative to the housing 150, and thus relative to the paddle member 140. An entirety of the insertion member 130 thus can be slid or translated relative to the housing 150 within the channel 153 in the downward direction. In particular, the insertion member 130 can be advanced in the downward direction until the abutment surface 139 of the handle 132 abuts or otherwise nests in the abutment surface 157 of the housing 150, at which point the insertion member 130 can be in a fully advanced position. It should be appreciated that the advancement force can be applied to the insertion member 130 as a manual force or an automatic force in any suitable alternative manner as desired.

As the insertion member 130 advances to the fully advanced position, the tip portion 133 similarly advances to a position beyond a lower most end of the paddle head 142. Thus, at least a portion of the insertion member 130 can be offset with respect to the paddle head 142 in the downward direction when the insertion member 130 is in the fully advanced position. In particular, the blade 135 can be offset with respect to the paddle head 142 in the downward direction. Further, the extension 131 is aligned with the paddle head 142 along a direction that is perpendicular to the first direction D1, such as the second direction D2. Accordingly, the reference line R1 that extends along a direction perpendicular to the first direction D1, such as the second direction D2, along a downward-most end of the paddle head 142 also passes through the extension 131 when the insertion member 130 is in the extended position. Desirably, the tip portion 133 can advance at least to a position aligned with the paddle head 142 along a direction perpendicular to the first direction, such as the second direction D2. As a result, the bone removal tool 120 can capture a bone sliver between the paddle head 42 and the insertion member 130, and in particular extension 131, as will now be described.

Figure 5A:
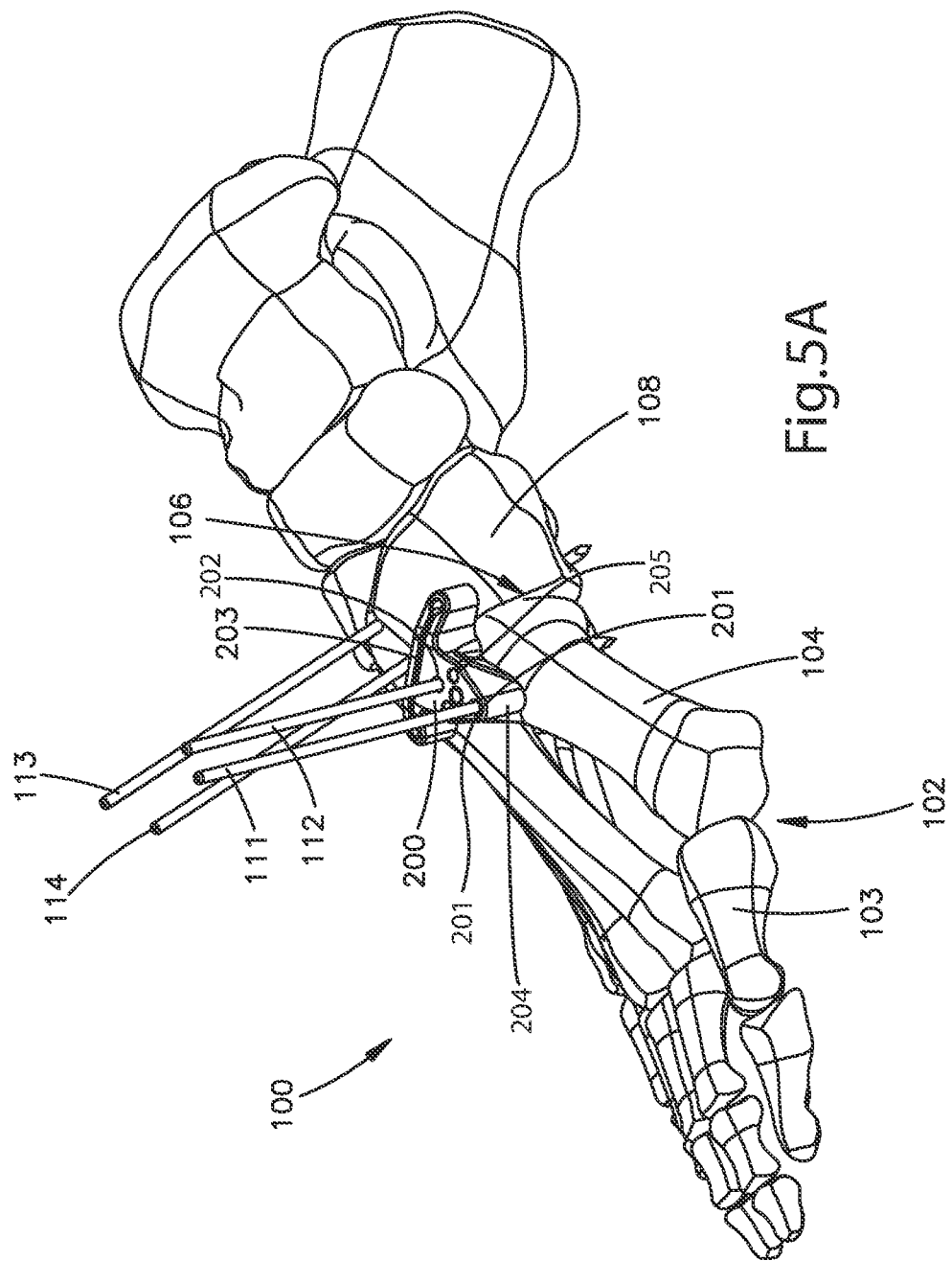
FIG. 5A is a perspective view of a patient's foot including a bunion deformity, showing a cut guide positioned to resect an end portion of a first metatarsal at a tarsometatarsal (TMT) joint between the first metatarsal and the cuneiform bone of the patient's foot.

Referring now to FIG. 5A, the patient's foot 100 is shown including the deformed condition shown as a bunion 102 in need of surgical correction. The bunion 102 can be located between the proximal phalanx 103 and the first metatarsal 104. The metatarsal 104 can form the TMT joint 106 with the cuneiform 108. It should be appreciated that while techniques and apparatus are described herein with respect to the TMT joint, the techniques and apparatus described herein can alternatively be used in conjunction with any joint between any two bones in the body. In this regard, the first metatarsal 104 can be referred to as a first bone, and the cuneiform 108 can be referred to as a second bone that define a joint therebetween.

With continuing reference to FIG. 5A, the deformity correction system can include at least one first or distal guide member or K-wire such as first and second guide members or K-wires 111 and 112, that can be driven into the metatarsal bone 104. The first and second K-wires 111 and 112 can be referred to as distal K-wires. The first K-wire 111 can be positioned distal of the second K-wire 112. That is, the second K-wire 112 can be positioned between the first K-wire 111 and the joint 106. The first K-wire 111 can thus be referred to as an outer distal K-wire, and the second K-wire 112 can be referred to as an inner distal K-wire. The K-wires 111 and 112 can be driven along a first K-wire insertion direction such as with the use of a guide, such as an alignment guide as described in U.S. Pat. No. 11,058,546, the entirety of which is hereby incorporated by reference for all purposes. The first and second K-wires 111 and 112 can be oriented parallel to each other, and spaced from each other along a first spacing direction.

The deformity correction system can further include at least one second or proximal guide member or K-wire, such as third and fourth guide or K-wires 113 and 114 that can be driven into the cuneiform 108. The third and fourth K-wires 113 and 114 can be referred to as proximal K-wires. The third K-wire 113 can be positioned proximal of the fourth K-wire 114. That is, the fourth K-wire 114 can be positioned between the third K-wire 113 and the joint 106. The third K-wire 113 can thus be referred to as an inner proximal K-wire, and the fourth K-wire 114 can be referred to as an outer proximal K-wire. The third and fourth k-wires 113 and 114 can be driven into the cuneiform 108 along a second K-wire insertion direction that is different from the first K-wire insertion direction. The third and fourth k-wires 113 and 114 can be oriented parallel to each other, and spaced from each other along a second spacing direction that is different than the first spacing direction. The third and fourth K-wires 113 and 114 can be inserted into the cuneiform 108 using a guide, such as an alignment guide as described in U.S. Pat. No. 11,058,546. After resection of the joint 106, the distal K-wires can be positionally changed with respect to the proximal K-wires so as to correspondingly positionally change the underlying first metatarsal 104 with respect to the medial cuneiform bone 108. In particular, the K-wires 111-114 can be received by respective apertures of a correction guide 300 (see FIG. 10) that drives the distal K-wires to positionally change from a first position shown in FIG. 5A to a corrected position shown in FIG. 10, thereby reducing or eliminating (i.e., correcting) the bunion 102, as described further in U.S. Pat. No. 11,058,546.

As shown in FIGS. 5A-6B, the joint 106 can be resected using a cut guide 200 and a cutting instrument 210. Thus, the deformity correction system can include the cut guide 200 and the cutting instrument 210. The cutting instrument 210 can be configured as an osteotome, bone saw, or other suitable cutting instrument as desired. The cut guide 200 can include a body 204 and a plurality of apertures, 205 such as first and second apertures 201 and 202 that extend through the body 204. The first and second apertures 201 and 202 can be configured to selectively receive the first and second proximal K-wires 111 and 112, respectively, and the first and second distal k-wires 113 and 114, respectively. The cut guide 200 can further define a cut slot 203 that extends through the body 204 at a location spaced from the first and second apertures 201 and 202. The cut slot 203 can be configured to receive and guide a cutting instrument 210 to resect the aligned cuneiform 108 or metatarsal 104, depending on which wires are received in the apertures 201-202.

Figure 5B:
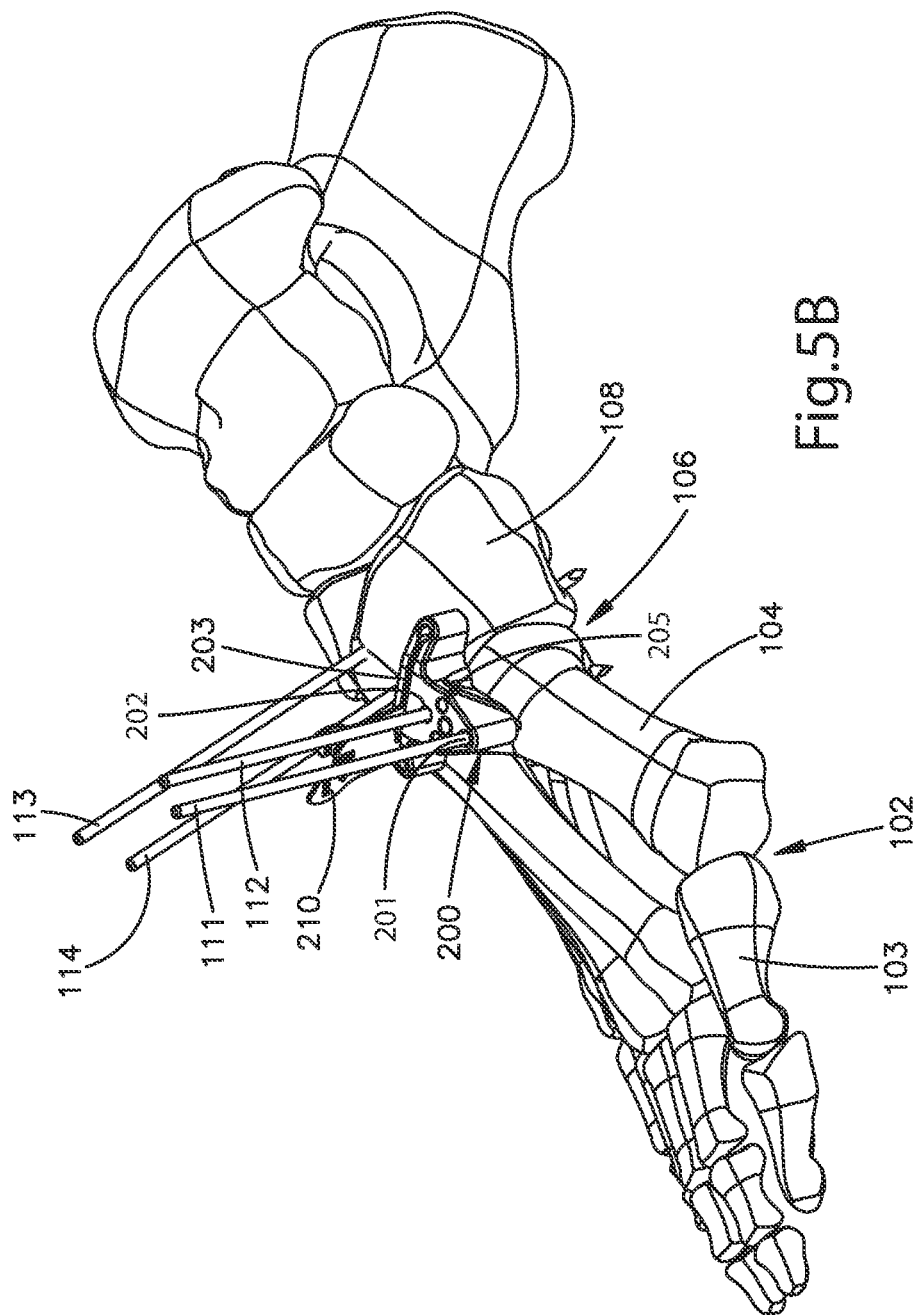
FIG. 5B is a perspective view of the patient's foot of FIG. 5A, but showing a cutting instrument inserted through a cut slot of the cut guide so as to resect the first metatarsal at the tarsometatarsal (TMT) joint, thereby creating a metatarsal sliver.

In particular, referring now to FIGS. 5A-5B, the cut guide 200 can be driven over the first and second K-wires 111 and 112, such that the first and second apertures 201 and 202 receive the first and second K-wires 111 and 112, respectively, that are inserted into the metatarsal 104. When the cut guide 200 receives the first and second K-wires 111 and 112, respectively, the cut slot 203 is aligned with the metatarsal 104 at a location that will separate a first or metatarsal end portion 105a of the metatarsal 104 from a remaining portion 105b of the first bone or metatarsal 104 (see FIG. 7B). The metatarsal end portion 105a that faces the joint 106. It should be appreciated that the cut guide 200 can include the plurality of apertures 205 greater than two apertures. In one example, the second aperture 202 can be selected from one of the plurality of apertures 205, such that the first and second apertures 201 and 202 are spaces as desired based on the patient's anatomy. The apertures 205 can be spaced in different locations that allow several options for aligning the cut slot 203 at a desired location of the metatarsal 104. Thus, the cut guide 200 is configured such that the first and second apertures 201 and 202 locate the cut slot 203 as desired based on the patient's anatomy when the first and second apertures 201 and 202 receive the first and second K-wires 111 and 112, respectively.

In particular, the cut guide 20 can be positioned such that the cut slot 203 is aligned with the metatarsal 104 at a first or distal select location that separates the metatarsal end portion 105a that is to be removed from a remaining portion 105b of the metatarsal 104. Thus, the cut slot is configured to receive the cutting instrument 210 and guide the cutting instrument 210 to cut the metatarsal 104 at the first or distal select location. Thus, the cutting instrument 210 can be inserted through the cut slot 203 and guided by the cut slot 203 to cut along the distal select location which can define a first or distal resection cut 109 (see FIG. 7A) that separates the metatarsal end portion 105a from the remaining portion 105b of the metatarsal 104. The cutting instrument 210 can cut to a depth sufficient such that an entirety of the metatarsal end portion 105a is separated from the remaining portion 105b. The separated metatarsal end portion 105a can define a first or distal bone sliver 107 (see FIG. 7B) of the joint 106.

Figure 6A:
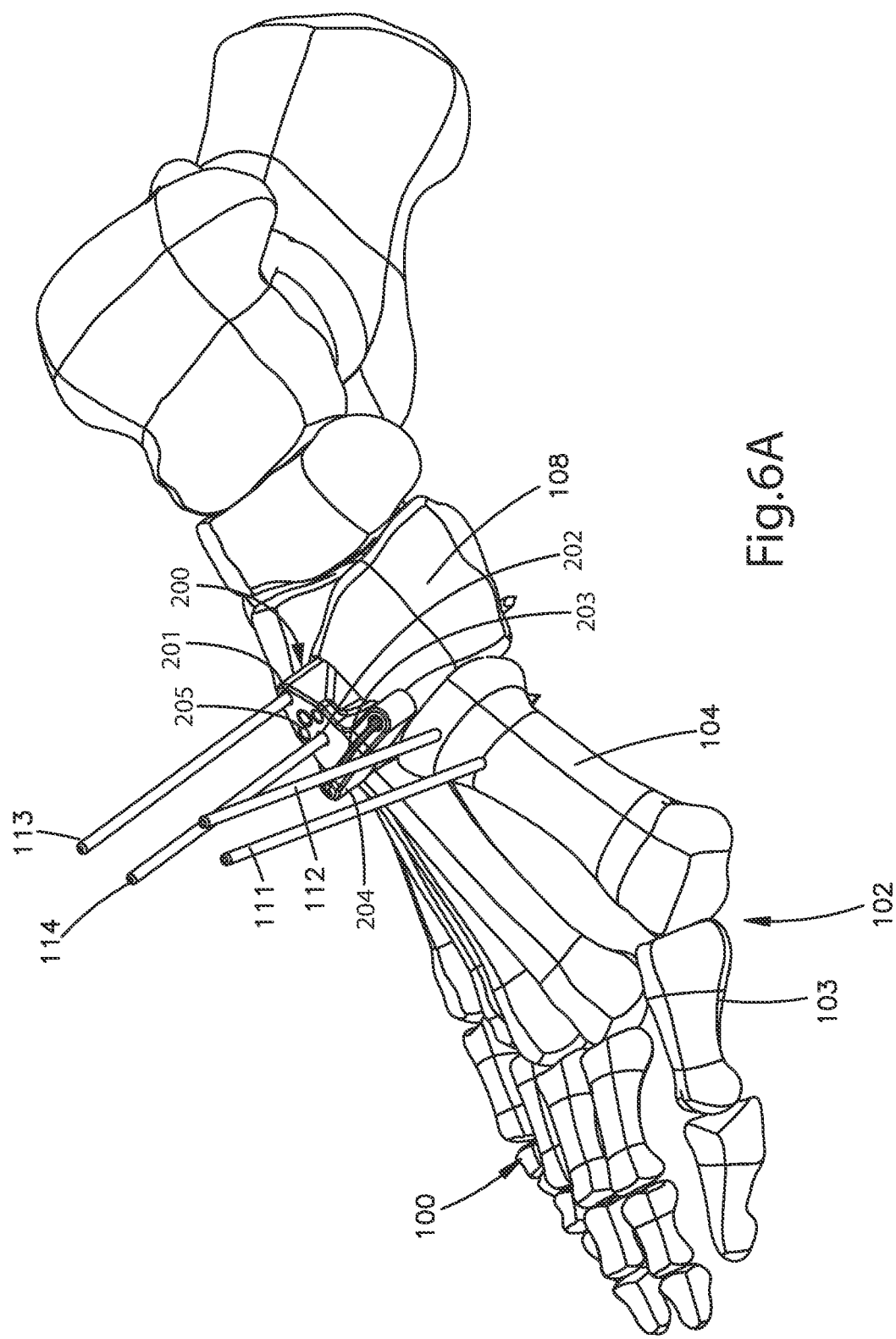
FIG. 6A is a perspective view of the patient's foot, showing the cut guide positioned to resect an end portion of the cuneiform bone at the tarsometatarsal (TMT) joint.
Figure 6B:
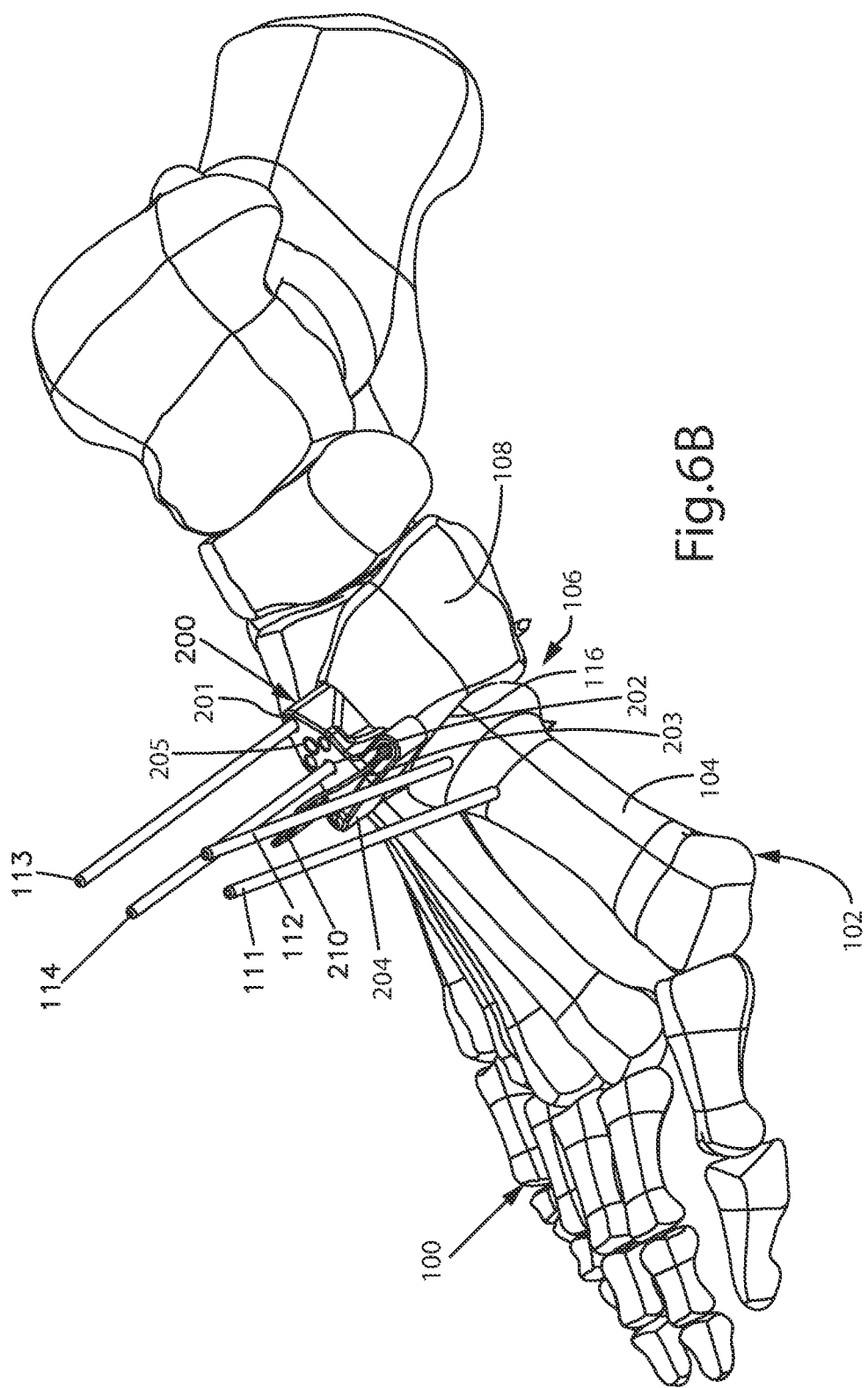
FIG. 6B is a perspective view of the patient's foot of FIG. 6A, but showing a cutting instrument inserted through a cut slot of the cut guide so as to resect the cuneiform bone at the tarsometatarsal (TMT) joint, thereby creating a cuneiform sliver.

Referring now to FIGS. 6A-6B, once the metatarsal 104 has been cut as described above, the cutting instrument 210 can be removed from the cut guide 200, and the cut guide 200 can be removed from the first and second K-wires 111 and 112. Next, the cut guide 200 can be inserted over the third and fourth K-wires 113 and 114 so as to align the cut slot 203 with the cuneiform 108 so as to separate a second or cuneiform end portion 115a of the second bone or cuneiform 108 with a remaining portion 115b of the cuneiform 108 (see FIG. 7B). The cuneiform end portion 115a can face the joint 106 in the manner described above with respect to the metatarsal end portion 105a.

In particular, the cut guide 200 can be driven over the third and fourth K-wires 113 and 114, such that the first and second apertures 201 and 202 receive the third and fourth K-wires 113 and 114, respectively, that are inserted into the cuneiform 108. When the cut guide 200 receives the third and fourth K-wires 113 and 114, respectively, the cut slot 203 is aligned with the cuneiform 108 at a location that will separate the cuneiform end portion 115a from the remaining portion 115b of the cuneiform 108. It should be appreciated that the cut guide 200 can include the plurality of apertures 205 greater than two apertures. In one example, the second aperture 202 can be selected from one of the plurality of apertures 205, such that the first and second apertures 201 and 202 are spaces as desired based on the patient's anatomy. The apertures 205 can be spaced in different locations that allow several options for aligning the cut slot 203 at a desired location of the cuneiform 108. Thus, the cut guide 200 is configured such that the first and second apertures 201 and 202 locate the cut slot 203 as desired based on the patient's anatomy when the first and second apertures 201 and 202 receive the third and fourth K-wires 113 and 114, respectively.

In particular, the cut guide 20 can be positioned such that the cut slot 203 is aligned with the cuneiform 108 at a second or proximal select location that separates the cuneiform end portion 115a that is to be removed from the remaining portion 115b of the cuneiform 108. Thus, the cut slot 203 is configured to receive the cutting instrument 210 and guide the cutting instrument 210 to cut the cuneiform 108 at the second or proximal select location. Thus, the cutting instrument 210 can be inserted through the cut slot 203 and guided by the cut slot 203 to cut along the proximal select location which can define a second or proximal resection cut 116 (see FIG. 7B) that separates the cuneiform end portion 115a from the remaining portion 115b of the cuneiform 108. The cutting instrument 210 can cut to a depth sufficient such that an entirety of the cuneiform end portion 115a is separated from the remaining portion 115b. The separated cuneiform end portion 115a can define a second or proximal bone sliver 117 (see FIG. 7B) of the joint 106.

While the cut guide 200 has been described as configured to selectively receive each of the distal K-wires 111-112 and the proximal K-wires 113-114 selectively, in another example a first cut guide can be configured to receive the distal K-wires 111-112 to align the cut slot with the metatarsal 104, and a second cut guide can be configured to receive the proximal K-wires 113-114 to align the cut slot with the cuneiform 108. While FIGS. 5A-6B show resection of the metatarsal 104 prior to resection of the cuneiform 108, it should be appreciated that the cuneiform 108 can alternatively be resected prior to the metatarsal 104. Further, while the same cutting instrument 210 can be used to resect the metatarsal 104 and the cuneiform 108 in one example, in another example different cutting instruments can be used to resect the metatarsal 104 and the cuneiform 108.

Figure 7A:
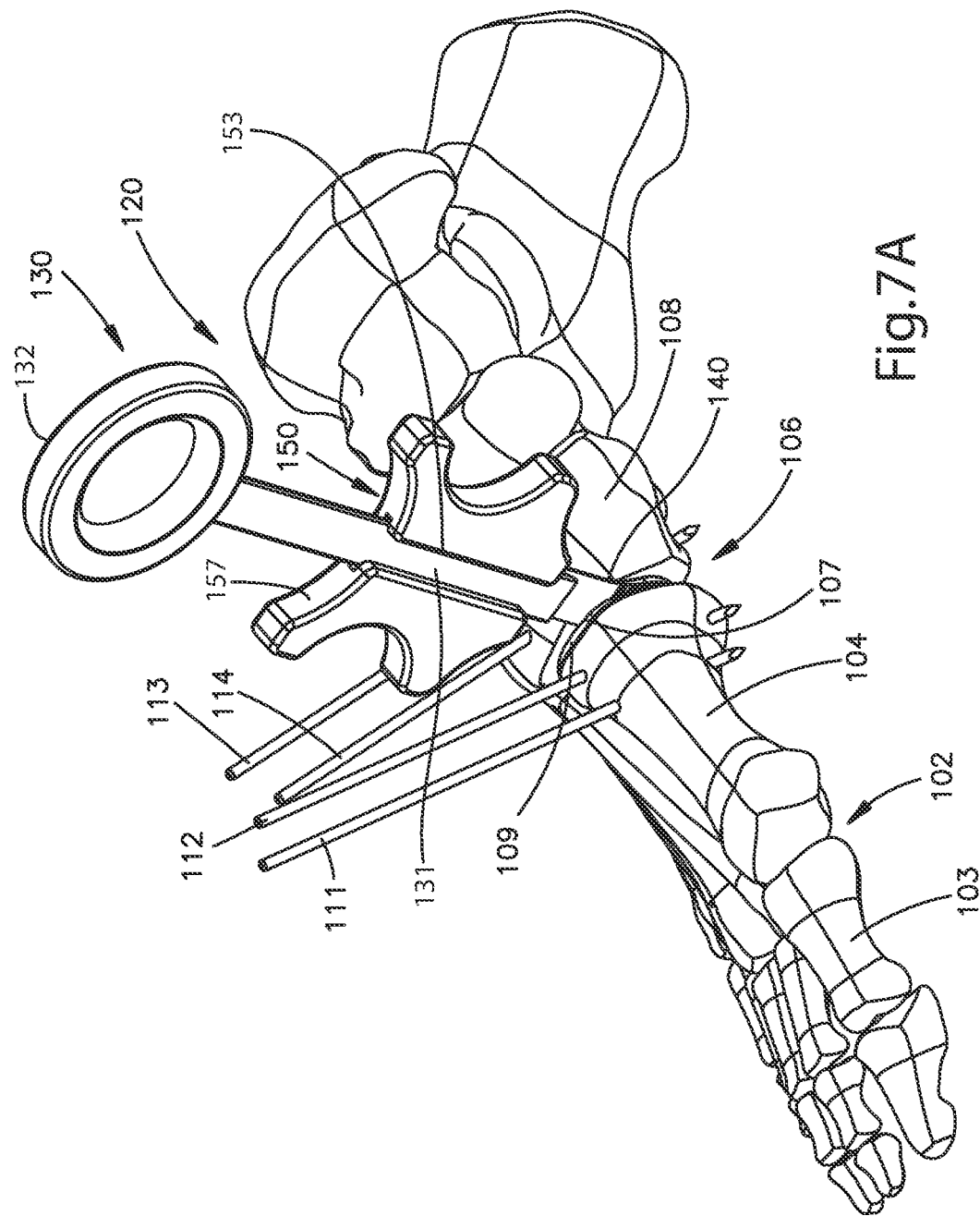
FIG. 7A is a perspective view the patient's foot of FIG. 6A, but showing the cut guide and cutting instrument removed, and of a paddle member of the bone removal tool inserted into the TMT joint with the insertion member in the retracted position.
Figure 7B:
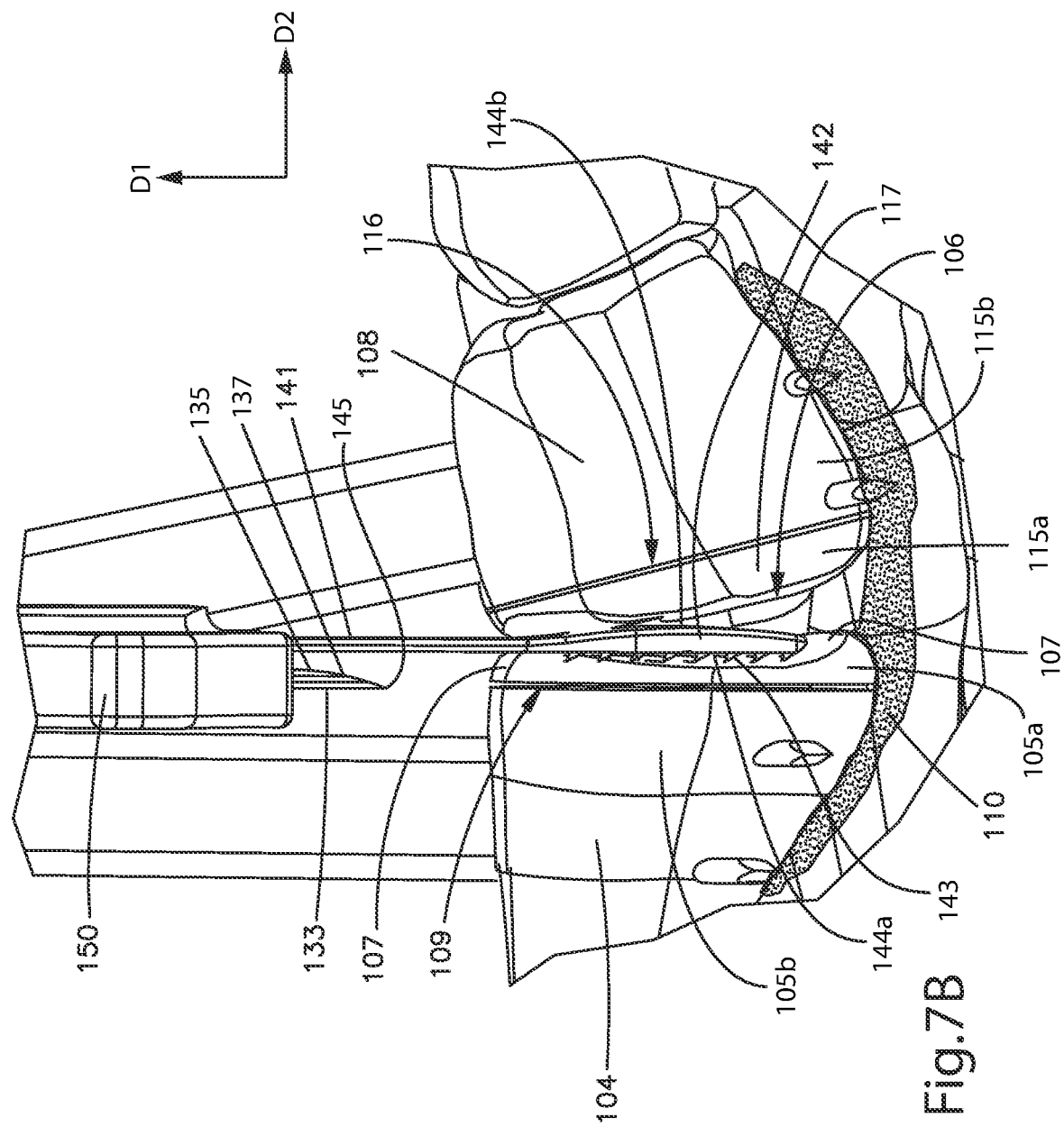
FIG. 7B is an enlarged side elevation view of the patient's foot showing the TMT joint of FIG. 7A.

Referring now to FIGS. 7A-7B, as described above the first or distal resection cut 109 can separate the first or distal bone sliver 107 from the remaining portion 105b of the metatarsal bone 104. The sliver 107 can be defined by the end portion of the metatarsal 104 as described above, and can remain in the joint 106. It is desirable to remove the sliver 107 from the joint 106 to provide ample space in the resected joint 106 to allow for positional manipulation of the metatarsal 104 relative to the cuneiform in order to correct the deformity. The bone removal tool 120 is configured to grasp the sliver 107 and remove the sliver 107 from the joint 106.

It is recognized that after the resection, the bone sliver 107 can remain attached with the remaining portion 105*b* of the metatarsal 104 by soft tissue, such as one or more ligaments, that form the joint 106. As one example, the plantar tarsometatarsal ligament 110 can extend across the joint 106 and join the metatarsal bone 104 to the cuneiform bone 108. The cutting operation that removes the metatarsal end portion 105*a* from the remaining portion 105*b* can also sever these one or more ligaments. However, in some instances it can be difficult to sever all of these ligaments because of the placement of the joint 106 and/or the location of the skin incision used to access the joint 106. Thus, the plantar tarsometatarsal ligament 100 can extend from the remaining portion 105*b* of the metatarsal 104 to the remaining portion 115*b* of the cuneiform 108 after the cutting operations have been completed. The plantar tarsometatarsal ligament 110 is generally located on a plantar side of the joint 106, while the skin incision is generally located on a dorsal side of the foot 100, making access to the plantar tarsometatarsal ligament 110 difficult. The bone removal tool 120 can further be configured to sever the plantar tarsometatarsal ligament 110.

During operation, the paddle member 140 can be inserted into the joint 106 such that the first major surface 144*a* faces the bone sliver to be removed. As illustrated in FIGS. 7A-7B, the bone sliver to be removed can be defined by the first or distal bone sliver 107. In particular, the paddle head 142 can be inserted into the joint 106 to a depth whereby the paddle head 142 is disposed between the bone sliver 107 and the cuneiform 108 along the second direction D2. Thus, the bone sliver 107 is disposed between the paddle head 142 and the remaining portion of the bone, which can be defined by the remaining portion 105*b* of the metatarsal 104. The paddle member 140 can be inserted into the joint 106 with the insertion member 130 in the retracted position. The retention features 143 on the head 142 can be oriented to facilitate insertion of the paddle head 142 into the tight joint space.

Figure 8A:
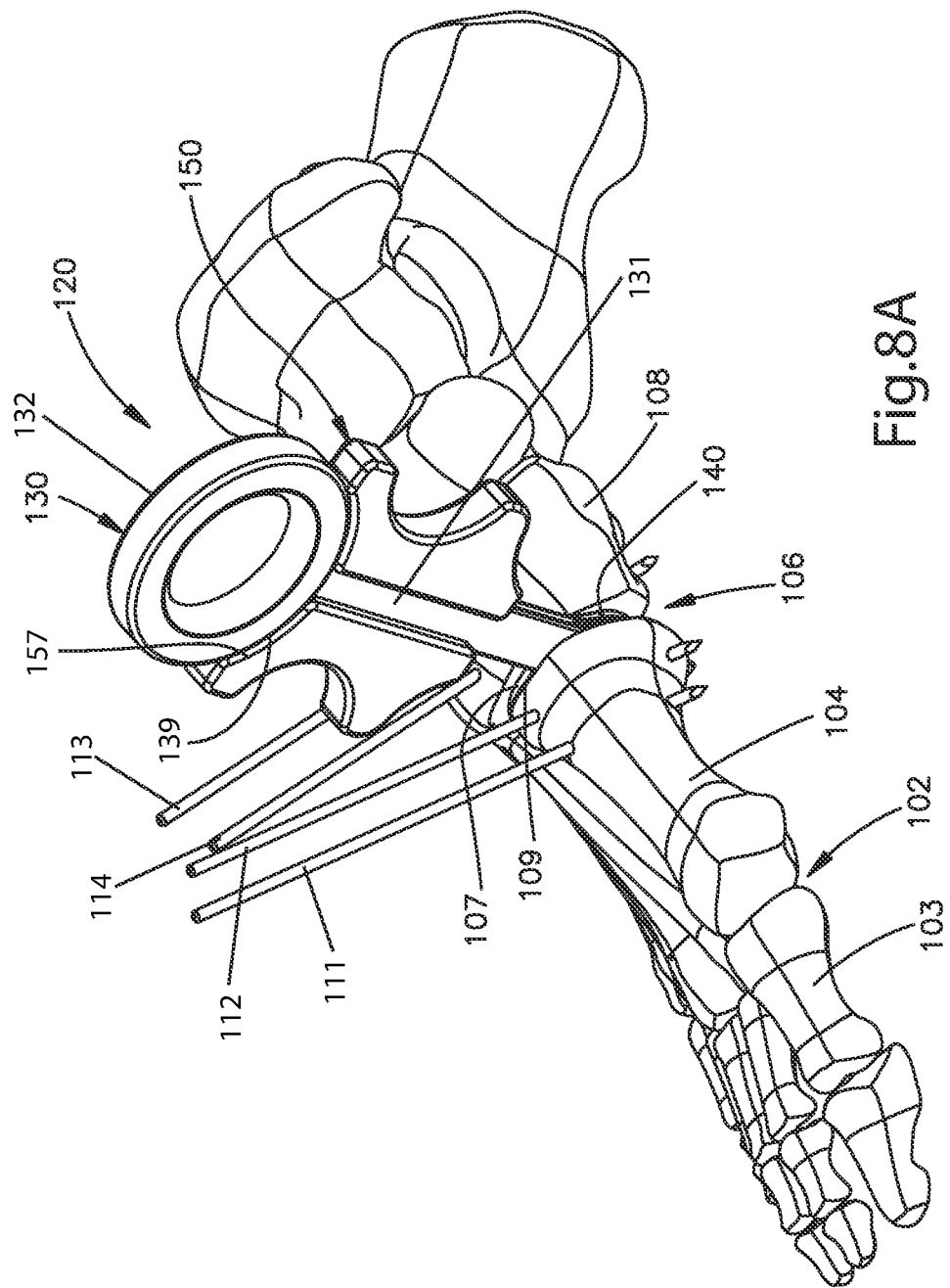
FIG. 8A is a perspective view of the patient's foot of FIG. 7A, but showing the insertion member in the advanced position in the TMT joint so as to capture the metatarsal sliver.

Referring now to FIGS. 8A-8B, after insertion of the paddle member 140 into the resected joint 106, the insertion member 130 can be driven into the resection cut which can be defined by the distal resection cut 109. In particular, the insertion member 130 can be advanced in the insertion direction into the distal resection cut 109. For instance, the insertion member 130 can be advanced from the retracted position in the insertion direction into the distal resection cut 109. In some examples, the insertion member 130 can be advanced to the advanced position. For instance, the insertion member 130 can be advanced to the fully advanced position. In other examples, the insertion member 130 can be advanced to a position that is advanced with respect to the retracted position, which can define the advanced position. The retention features 143 of the head 142 can aid in advancing of the insertion member 130 into the resection cut 109 without inadvertently removing the paddle member 140 from the resected joint 106. In particular, the retention features 143 can grip the bone sliver 107, stabilizes the housing 50 to provide a counterforce against the insertion force applied to the insertion member 130 that drives the insertion member into the resection cut 109. It is also appreciated that the gripping the bone sliver 107 by the retention features can prevent the bone sliver 107 from inadvertently slipping out of the space between the insertion member 130 and the paddle head 142.

In one example, the extension 131 of the insertion member 130 can be extended to a depth whereby the blade 135 is aligned with the paddle head 142 along the second direction D2. The offset distance R2 (FIGS. 3A-3B) from the insertion member 130, and in particular the extension 131, to the paddle shaft 141 or the paddle head 142 (depending on the position of the insertion member 130) in the second direction D2 can be less than the thickness of the bone sliver 107 in the second direction D2 in some examples. At least one or both of the shaft 141 of the paddle member 140 and the extension 131 of the insertion member 130 can be flexible relative to the other of the shaft 141 of the paddle member 140 and the extension of 131 of the insertion member 130. Alternatively or additionally, the retention features 143 can be flexible relative to the first major surface 144*a* of the paddle head 142, and thus relative to the extension 131 of the insertion member 130. Thus, it can be said that one of the insertion member 130 and the paddle member 140 can be flexible with respect to the other of the insertion member 130 and the paddle member 140. In one example, the paddle member 140 (e.g., either or both of the paddle shaft 141 and the retention features 143) is flexible with respect to the extension 131 such that the lateral position of the blade 135 along the second direction D2 remains substantially constant as it is inserted into the resection cut 109. In other examples, the retention features 143 can be rigid.

In one example, the distance from the tip 145 to the paddle shaft 141 or the paddle head 142 (depending on the position of the insertion member 130) in the second direction D2 can be equal to or greater than the thickness of the bone sliver 107 in the second direction D2. Thus, as the extension 131 is inserted into the resection cut 109, the tip 145 is inserted into the resection cut 109, and the bone sliver 107 can ride along the bevel 137 as the extension 131 is further inserted into the resection cut 109. As the bone sliver 107 rides along the bevel 137, either or both of the insertion member 130 and the paddle member 140 can resiliently flex away from the other of the insertion member 130 and the paddle member 140. In other examples, either or both of the extension 131 and the paddle shaft 141 can be manually deflected away from the other of the extension 131 and the paddle shaft 141 so as to provide clearance that allows the tip 145 to be inserted in the resection cut 109 and place the bone sliver 107 between the extension 131 and the paddle head 142. Therefore, the bone sliver 107 can be captured in a retention space 146 between the insertion member 130, and in particular the extension 131, and the paddle member 140, and in particular the paddle head 142. The insertion member 130, and in particular the extension 131, and the paddle member 140, and in particular the paddle head 142, can cooperate to apply a normal retention force against the bone sliver 107 that retains the bone sliver 107 in the retention space 146. When the paddle shaft 141 is flexible, the bone sliver 107 can cause the paddle shaft 141 to flex as the bone sliver 107 rides along the bevel 137, which displaces the paddle head 142 outwardly along the second direction D2 away from the extension 131.

In some examples, the extension 131 can be advanced until the tip portion 133 can be aligned with the paddle head 142 along the second direction D2, such that the bone sliver 107 is captured between the tip portion 133 and the paddle head 142. The bone removal tool 120, including the insertion member 130 and the paddle member 140 can then be removed from the patient's foot 100 in the removal direction so as to remove the sliver 107 from the resected joint 106 (see, e.g., FIGS. 9A-9B). Alternatively, the extension 131 can be advanced until the tip portion 133 is offset with respect to the paddle head 142 in the insertion direction, such that the bone sliver 107 is captured between the extension 131 and the paddle head 142 prior to removing the bone removal tool 120 from the patient's foot.

In some instances, it may be desirable to sever the plantar tarsometatarsal ligament 110 with the bone removal tool 120, for example when the plantar tarsometatarsal ligament was not severed during resection of the joint 106. Advancement of the extension 131 such that the tip portion 133 travels past the paddle head 142 in the insertion direction can cause the tip 145 and blade 135 to sever the tarsometatarsal ligament 110 at a location adjacent the bone sliver 107. It is also recognized that in some circumstances, the bone sliver 107 is not fully separated from the remaining portion 105b of the metatarsal 104. In such instances, advancement of the extension 131 can cause the tip 145 and the blade 135 to fully separate the bone sliver 107 from the remaining portion 105b of the metatarsal 104. It is recognized that the bone sliver 107 remains captured between the paddle head 142 and the extension 131 after the tarsometatarsal ligament 110 has been severed. Severance of the one or more ligaments, such as the tarsometatarsal ligament 110, can aid in the removal of the sliver 107 from the joint 106.

Figure 9A:
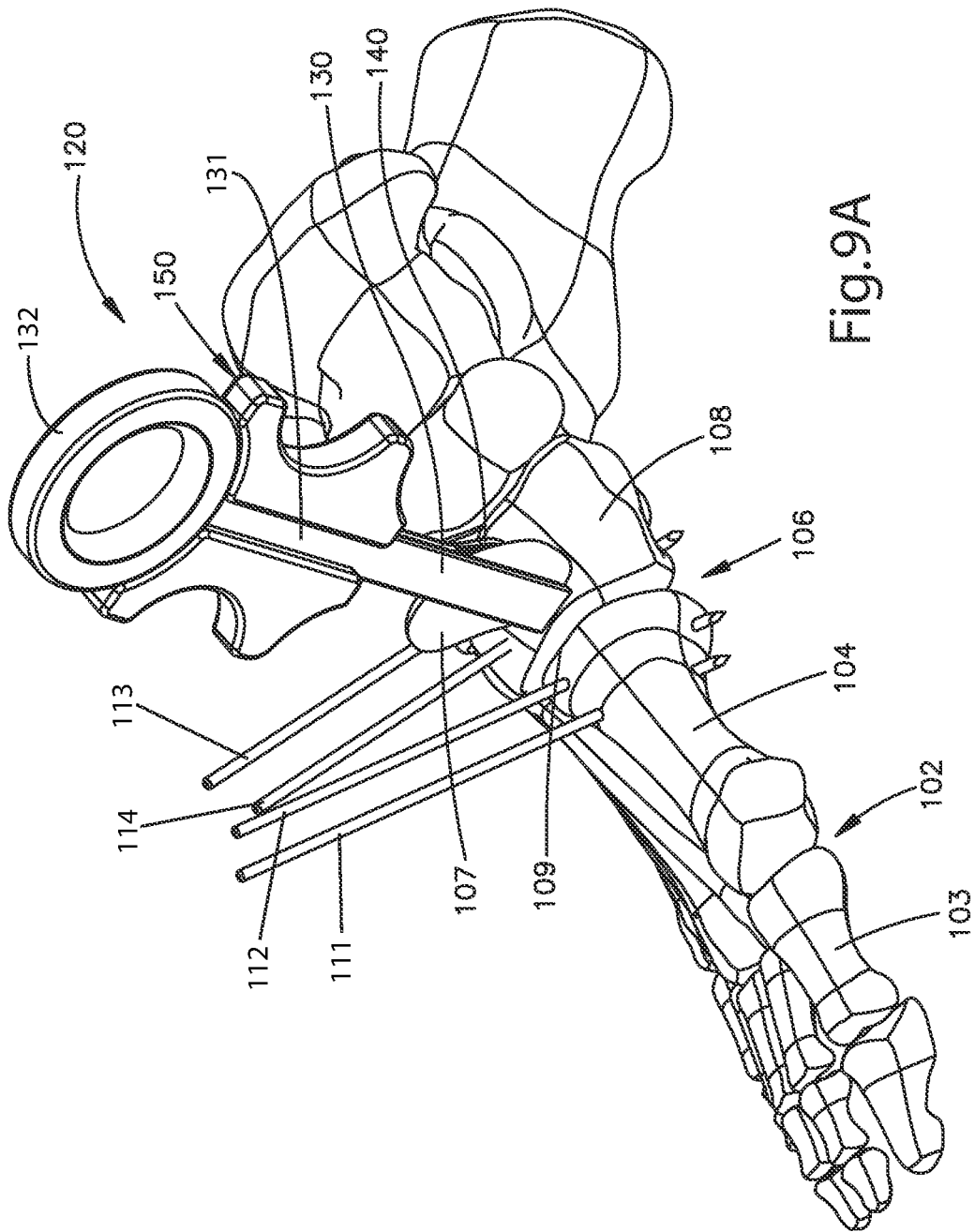
FIG. 9A is a perspective view of the patient's foot of FIG. 8A, but showing the removal tool coupled to the metatarsal sliver and removed from the TMT joint, thereby removing the metatarsal sliver from the TMT joint.
Figure 9B:
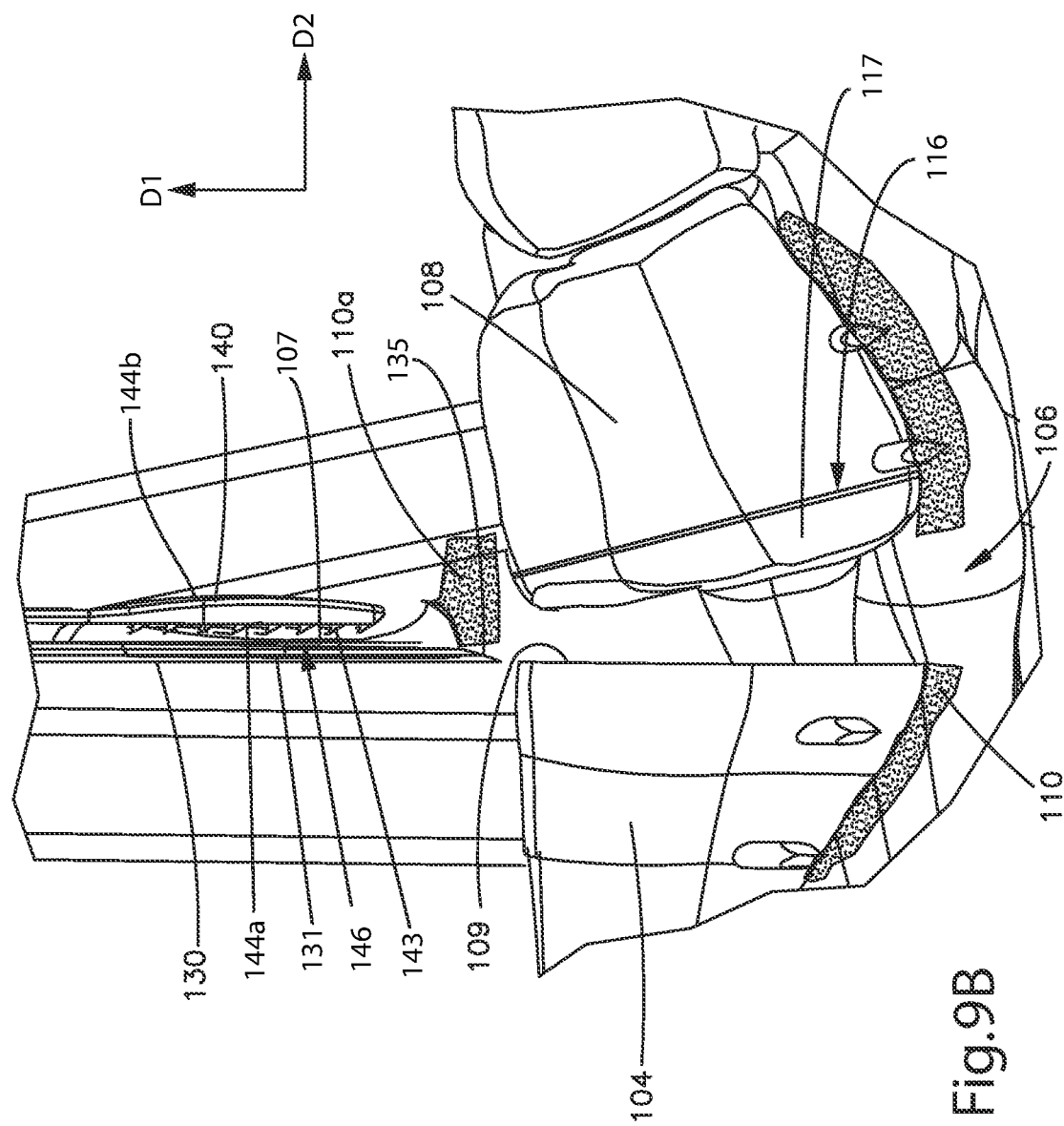
FIG. 9B is an enlarged side elevation view of the patient's foot showing the TMT joint of FIG. 9A.
Figure 9C:
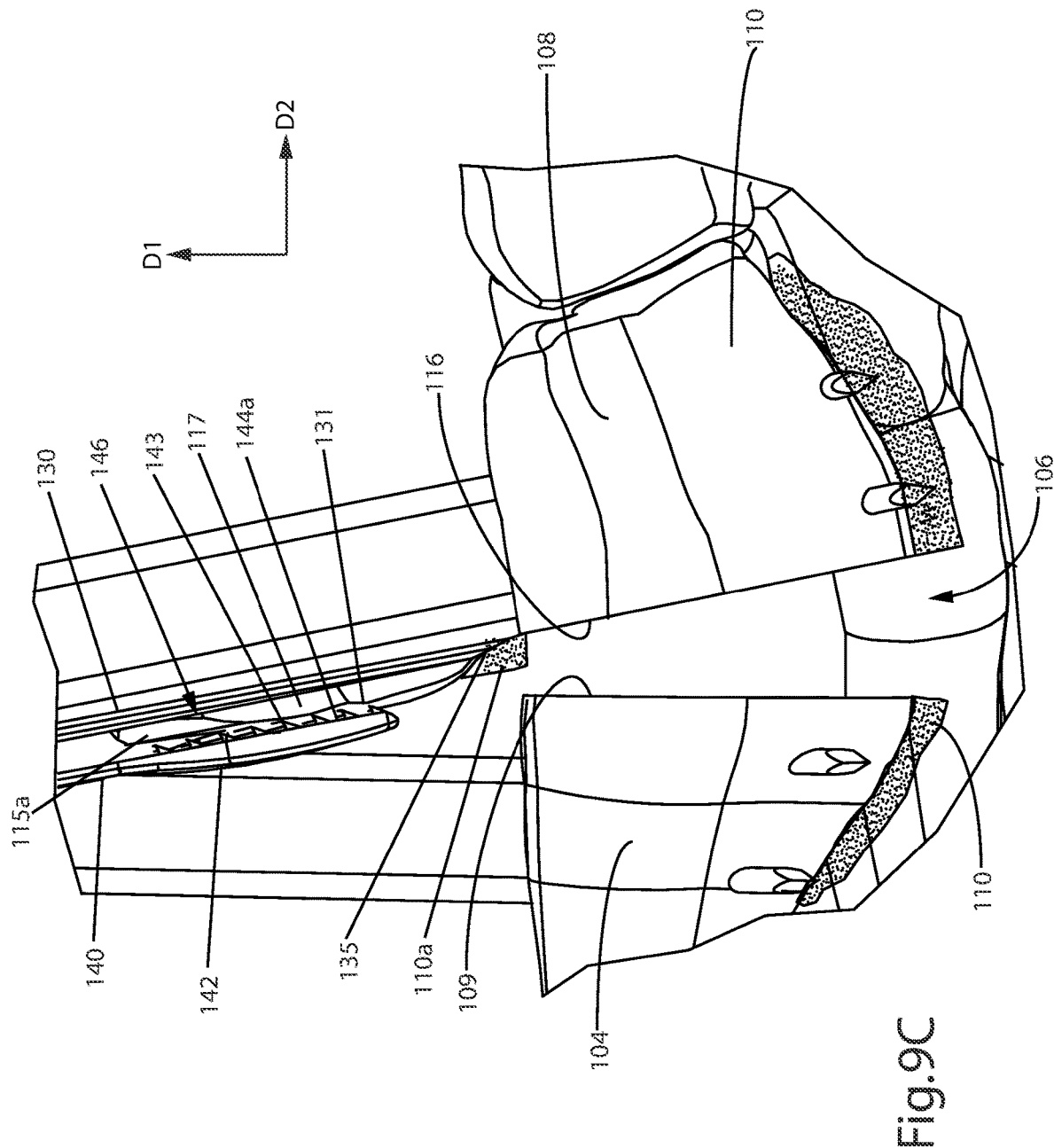
FIG. 9C is an enlarged side elevation view of the patient's foot similar to FIG. 3A, but showing removal of a bone sliver defined by a resected end portion of the cuneiform.

Referring now to FIGS. 9A-9B in particular, once the bone sliver 107 is captured in the retention space 146, the bone removal tool 102 can be removed from the resected joint 106, thereby removing the bone sliver 107 from the resected joint 106. Thus, when the bone sliver is defined by the metatarsal end portion 105a, the remaining end portion 105b of the metatarsal 104 can face or at partially define the resected joint 106. In particular, the insertion member 130, the paddle member 140, and the housing 150 can all be moved in the removal direction from the patient's foot 100. The insertion member 130 and the paddle member 140 carry the captured bone sliver 107 from the resected joint 106. In situations where the plantar tarsometatarsal ligament 110 was severed at a location adjacent the bone sliver 107, removal of the bone sliver 107 can cause another location of the ligament 110 to be severed. In particular, manipulation of the bone sliver 107 can cause the ligament 110 to stretch and twist until the ligament is torn 110, thereby freeing the bone sliver 107 from the patient's foot 100. The bone sliver 107 is then removed along with a resected portion 110a of the ligament 110 from the patient's foot in the manner described above. Alternatively, any suitable supplemental cutting instrument can sever the other location of the ligament 100 so as to free the bone sliver 107 from the patient's foot 100.

FIGS. 7A-9B show removal of the distal bone sliver 107. The steps associated with removal of the distal bone sliver 107 can be repeated for the proximal bone sliver 117, which is opposite the distal bone sliver 107 along the second direction. Thus, as shown at FIG. 9C, the proximal bone sliver 117 can be captured in the retention space 146 and removed from the from the patient's foot 100 in the manner described above with respect to the distal bone sliver 107. The proximal bone sliver 117 can be removed using the same removal tool 120 or a second removal tool 120. In particular, paddle head 142 is inserted into the joint 106 between the proximal bone sliver 117 and the first bone 104, such that the first major surface 144a of the paddle head 142 faces the bone sliver 117. The extension 131 of the insertion member 130 can be inserted between the proximal bone sliver 117 and the remaining portion 115b of the cuneiform 108, thereby capturing the proximal bone sliver 117 in the retention space 146 in the manner described above with respect to the distal bone sliver 107. At least one ligament such as the plantar tarsometatarsal ligament 110 can be severed adjacent the proximal bone sliver 117 in the manner described above as desired. It should be appreciated that the distal bone sliver 107 can be removed prior to removing the proximal bone sliver 117, or the proximal bone sliver 117 can be removed prior to removing the distal bone sliver 107. The remaining portion 115b of the cuneiform 108 can thus face or partially define the resected joint 106. The remaining portions 105b and 115b cooperate to define the resected joint 106.

Figure 10:
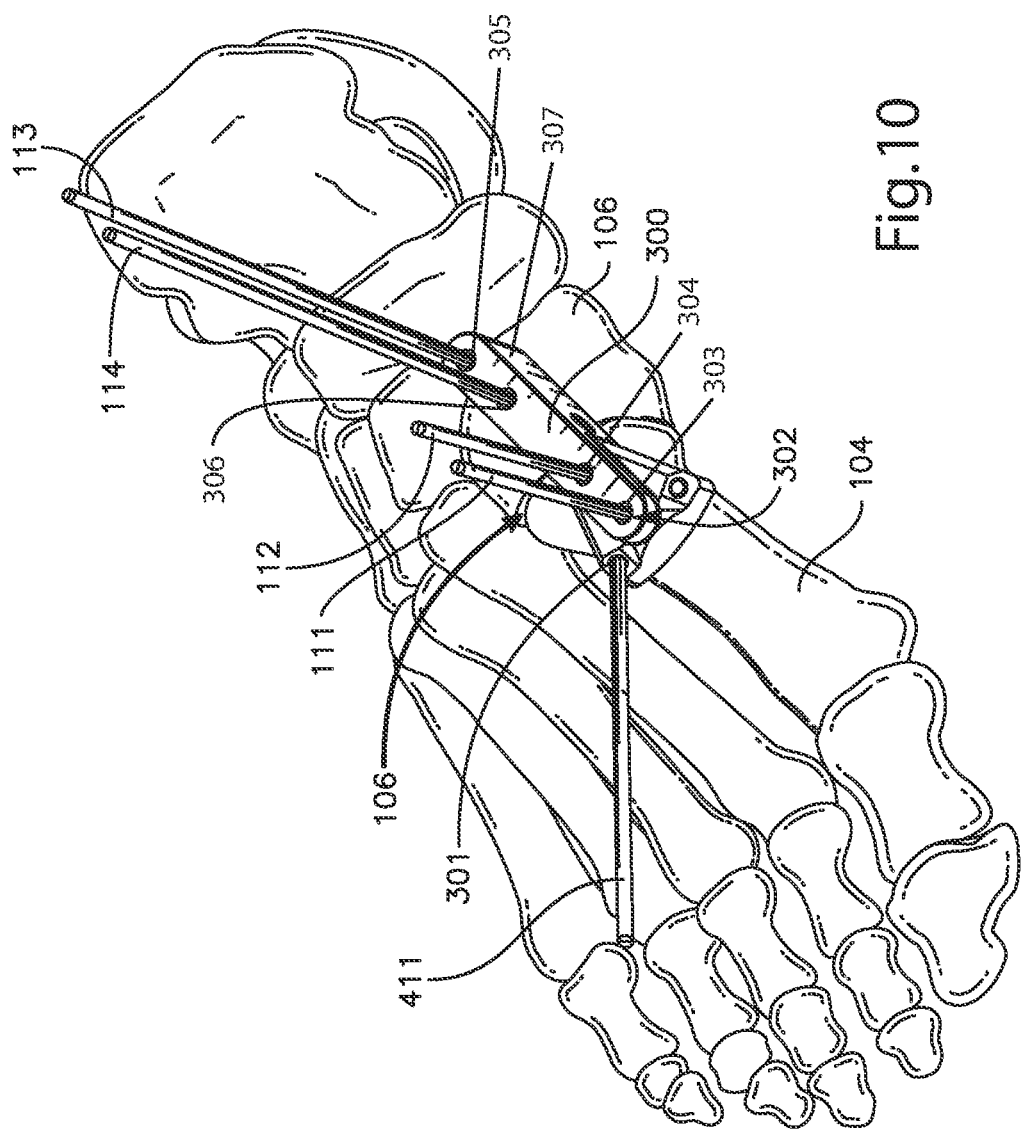
FIG. 10 is a perspective view of the patient's foot showing correction of the bunion using a correction guide inserted over a plurality of wires within the first metatarsal and the cuneiform bone.

Referring now to FIG. 10, once the bone slivers 107 and 117 have been removed, sufficient space exists in the resected joint 106 to allow for the metatarsal 104 to be positionally adjusted to correct the deformity. The correction system can further include a correction guide 300 that can be inserted over the K-wires 111-114 to drive the metatarsal 104 to move from a deformed position to a corrected position that adjusts an angle between the metatarsal 104 and the cuneiform 108, correcting the bunion 102. The correction guide 300 includes a correction body 307, and a plurality of guide apertures 302 that extend through the correction body 307. The guide apertures 302 can be sized and shaped to receive respective ones of the K-wires 111-114 so as to positionally adjust the metatarsal 104 with respect to the cuneiform.

In particular, the guide apertures 302 can include at least one first or distal guide aperture such as first and second guide apertures 303 and 304 that extend through the guide body 307. The first and second guide apertures 303 and 304 can be oriented parallel to each other. The first and second guide apertures 303 and 304 can be referred to as distal guide apertures. The guide aperture 303 can be positioned distal of the guide aperture 304. The first guide aperture 303 can thus be referred to as an outer distal guide aperture, and the second guide aperture 304 can be referred to as an inner distal guide aperture. The first guide aperture 303 is configured to receive the first K-wire 111, and the second guide aperture 304 is configured to receive the second K-wire 112.

The guide apertures 302 can further include at least one second or proximal guide aperture, such as third and fourth guide apertures 305 and 306 that extend through the guide body 307. The first and second guide apertures 303 and 304 can be oriented parallel to each other. The third and fourth guide apertures 305 and 306 can be referred to as proximal guide apertures. The third guide aperture 305 can be positioned proximal of the fourth guide aperture 306. The third guide aperture 305 can thus be referred to as an outer proximal guide aperture, and the fourth guide aperture 306 can be referred to as an inner proximal guide aperture. The third guide aperture 305 is configured to receive the third K-wire 113, and the fourth guide aperture 306 is configured to receive the fourth K-wire 114.

The guide apertures 302 can be sized substantially equal to the received ones of the K-wires 111-114. Further, the proximal apertures and the distal apertures can have a spatial relationship with respect to each other that is different than the spatial relationship between the proximal k-wires and the distal k-wires. For instance, in one example, the guide apertures 302 can all be aligned with each other along the guide body 307. In other examples, the first and second guide apertures 303-304 can be spaced from each other along a first aperture spacing direction, and the third and fourth guide apertures 305-306 are spaced from each other along a second aperture spacing direction that is angularly offset with respect to the first aperture spacing direction. Further, the guide apertures 302 can all be oriented parallel with each other. It will thus be appreciated that the guide apertures 302 can be arranged along the guide body 307 such the distal K-wires are repositioned to fit in the distal guide apertures when the proximal K-wires are disposed in the proximal guide apertures. Repositioning the distal K-wires correspondingly repositions that metatarsal 104 with respect to the cuneiform 108. In one example, the metatarsal 104 angulates in the frontal plane with respect to the cuneiform 108. The alignment guide 300 is further described in U.S. Pat. No. 11,058,546, the entirety of which is hereby incorporated by reference for all purposes. In another example, the apertures 302 can cause a realignment of the metatarsal 104 and the cuneiform 108 and/or compression between the metatarsal 104 and the cuneiform 108 into the corrected configuration. An example correction guide is the compressor block described in U.S. Pat. Pub. No. 2021/0251670, the entirety of which is hereby incorporated by reference for all purposes.

The correction guide 300 can also include one or more cross-pin holes 301 that is configured to receive a respective one or more fixing member such as fixing K-wires 411 that temporarily or permanently secures the joint 106 in the corrected configuration. The correction system can thus further include the one or more fixing K-wires 411. The fixing K-wire 411 can be driven through the cross-pin hole 301, through the metatarsal 104, and into the cuneiform 108. Thus, the cross-pin hole 301 maintains the metatarsal 104 in the corrected realigned position. The correction guide 300 can then be removed by removing the k-wires 111-112 and 113-114 from the metatarsal 104 and cuneiform 108, respectively, and further from the correction guide 300. Next, the correction guide 300 can be removed from the fixing k-wire 411 by sliding the correction guide 300 along the fixing K-wire 411 away from the patient's foot 100 until the correction guide 300 has been removed from the fixing K-wire 411.

Figure 11:
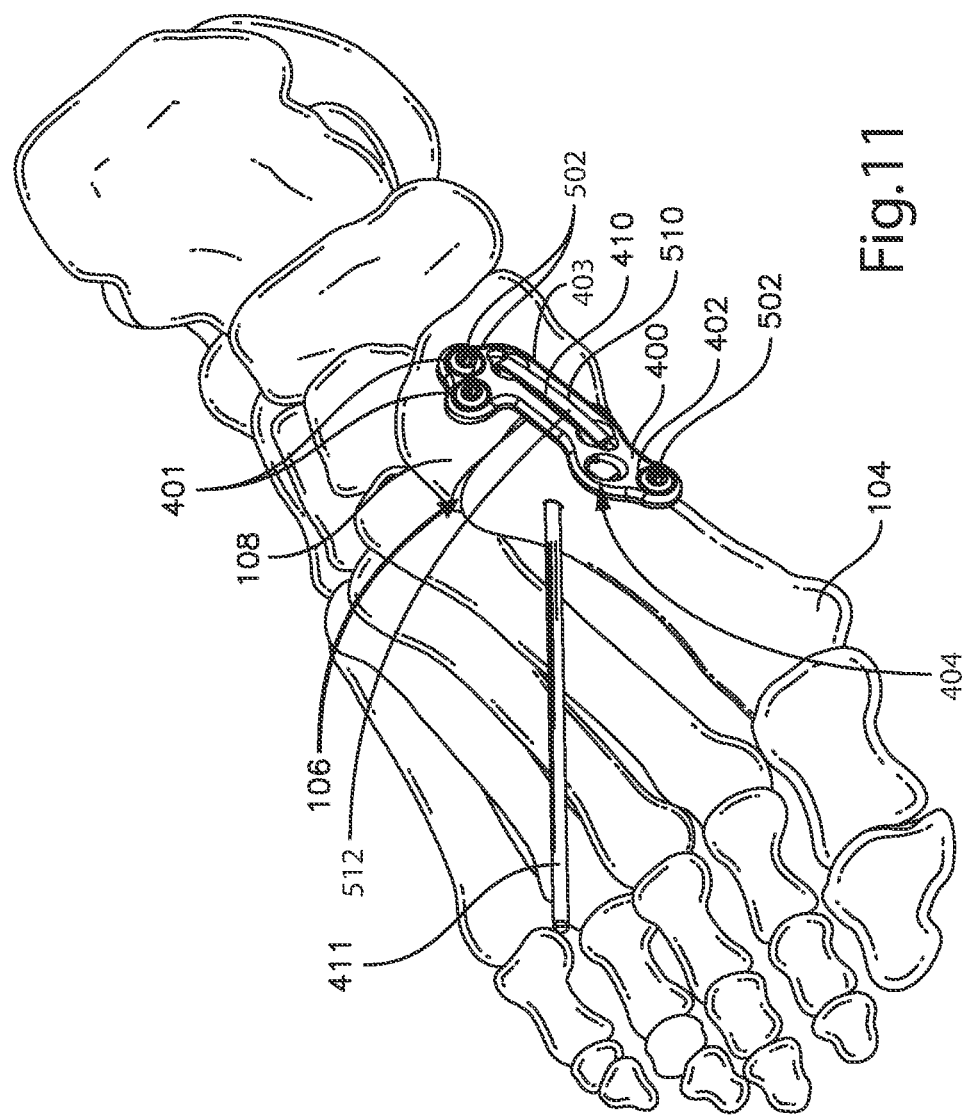
FIG. 11 is a perspective view of the patient's foot showing fusing of the TMT joint with the addition of a bone plate.

As shown in FIG. 11, the correction system can further include a bone fixation implant or plate 400 that is configured to be fixed to the repositioned metatarsal 104 and the cuneiform 108 across the resected joint, thereby fixing the metatarsal 104 in the realigned position. The fixing plate 400 can include a plate body 403 and a plurality of fixation apertures 404 that extend through the plate body 403. In particular, the fixation apertures 404 can include at least one first or proximal fixation aperture 401 such as a pair of proximal fixation apertures 401 that extend through the plate body 403. The fixation apertures 404 can further include at least one second or distal fixation aperture 402 that extends through the plate body 403. The bone plate 400 can be positioned on the patient's foot 100 such that the at least one proximal fixation aperture 401 is aligned with the cuneiform 108, and the at least one distal fixation aperture 402 is aligned with the repositioned metatarsal 104.

The fixation apertures are configured to receive bone fixation members such as bone screws 502. In particular, at least one bone screw 502 can be driven through a respective at least one of the at least one proximal fixation aperture 401 and into the cuneiform 108, and at least one bone screw 502 can be driven through a respective at least one of the at least one distal fixation aperture 402 and into the metatarsal 104. Thus, the fixation plate 400 permanently positionally stabilizes the metatarsal 104 with respect to the cuneiform 108, thereby allowing the resected joint 106 to fuse.

The fixation plate 400 can include any number of fixation apertures 404 as desired. Alternatively or additionally, the fixation plate 400 can be configured to receive a compression staple 510. In particular, the fixation plate 400 can include first and second staple apertures 407 and 408, respectively, that extend through the plate body 403. The first staple aperture 407 can be a proximal staple aperture that extends through the plate body 403 in alignment with the cuneiform 108. The second staple aperture 408 can be a distal staple aperture that extends through the plate body 403 in alignment with the metatarsal 104. The first and second staple apertures 407 and 408 can receive first and second legs, respectively, of the compression staple 510. The compression staple 510 can include a bridge 512 that extends from the first leg to the second leg. Thus, the bridge 512 can span the resected joint 106. The legs of the staple can be biased toward each other so as to provide compression across the resected joint 106. The fixation plate 400 is described in U.S. Pat. No. 11,058,546 and U.S. Pat. Pub. No. 2021/0251670, which are hereby incorporated by reference for all purposes. Once the bone fixation plate 400 has been fixed to the metatarsal 104 and the cuneiform 108, the fixing K-wire 411 can be removed from the patient's foot 100.

Certain Terminology

Terms of orientation used herein, such as "top," "bottom," "proximal," "distal," "longitudinal," "lateral," and "end," are used in the context of the illustrated example. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain examples include or do not include, certain features, elements, and/or steps. Thus, such conditional language is not generally intended to imply that features, elements, and/or steps are in any way required for one or more examples.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain examples require the presence of at least one of X, at least one of Y, and at least one of Z.

As used herein, the singular forms "a," "an," and "the" can include the plural unless indicated otherwise. The term "plurality", as used herein, means more than one, and reference to a plurality herein can be used with equal force and effect to the singular. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

The terms "approximately," "about," and "substantially" as used herein represent an amount close to the stated amount that still performs a desired function or achieves a desired result. For example, in some examples, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain examples, as the context may dictate, the term "generally parallel" can refer to something that departs from exactly parallel by less than or equal to 20 degrees. All ranges are inclusive of endpoints.

SUMMARY

Several illustrative examples of surgical instruments have been disclosed. Although this disclosure has been described in terms of certain illustrative examples and uses, other examples and other uses, including examples and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various examples. All possible combinations and subcombinations of elements and components described herein are intended to be included in this disclosure. No single feature or group of features is necessary or indispensable.

Certain features that are described in this disclosure in the context of separate implementations can also be implemented in combination in a single implementation. Conversely, various features that are described in the context of a single implementation also can be implemented in multiple implementations separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one example in this disclosure can be combined or used with (or instead of) any other portion of any of the steps, processes, structures, and/or devices disclosed or illustrated in a different example or flowchart. The examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative examples have been described, any examples having equivalent elements, modifications, omissions, and/or combinations are also within the scope of this disclosure. Moreover, although certain aspects, advantages, and novel features are described herein, not necessarily all such advantages may be achieved in accordance with any particular example. For example, some examples within the scope of this disclosure achieve one advantage, or a group of advantages, as taught herein without necessarily achieving other advantages taught or suggested herein. Further, some examples may achieve different advantages than those taught or suggested herein.

Some examples have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various examples can be used in all other examples set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular example of the inventions disclosed herein. No aspects of this disclosure are essential or indispensable. In many examples, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the examples described and illustrated in the figures. Many implementation variations are possible. Any of the features, structures, steps, or processes disclosed in this specification can be included in any example.

In summary, various examples of surgical instruments and related methods have been disclosed. This disclosure extends beyond the specifically disclosed examples to other alternative examples and/or other uses of the examples, as well as to certain modifications and equivalents thereof. Moreover, this disclosure expressly contemplates that various features and aspects of the disclosed examples can be combined with, or substituted for, one another. Accordingly, the scope of this disclosure should not be limited by the particular disclosed examples described above, but should be determined only by a fair reading of the claims.

What is claimed is:

1. A method of correcting alignment between a first and second bones across a joint, the method comprising the steps of:
    cutting the first bone so as to define a first end portion and a remaining bone portion of the first bone separated from each other by a resection cut, wherein the first end portion faces the joint;

driving a paddle member of a removal tool along a direction of insertion into the joint between the first end portion and the second bone, such that a paddle head of the paddle member faces the first end portion;

driving an insertion member of the removal tool along the direction of insertion into the resection cut, such that the first end portion is captured between the insertion member and the paddle head; and removing the first end portion from the joint while the first end portion is captured between the insertion member and the paddle head.

2. The method of claim 1, wherein the step of driving the insertion member causes retention features of the paddle member to bear against the first end portion.

3. The method of claim 2, wherein the retention features extend in a direction opposite the insertion direction as they project out from a surface of the paddle member.

4. The method of claim 3, wherein the insertion member comprises an extension that is spaced from the paddle head along a second direction that is less than a thickness of the first end portion, and the insertion member defines a blade having a bevel that extends to a tip, such that the tip is spaced from the paddle a distance that is greater than the thickness of the first end portion, wherein the second direction is perpendicular to the insertion direction.

5. The method of claim 4, wherein one of the insertion member and the paddle member is flexible so as to provide a normal retention force against the first end portion.

6. The method of claim 1, wherein the step of driving the insertion member comprises causing a cutting tip of the insertion member travel past the paddle head.

7. The method of claim 6, wherein the step of driving the insertion member causes the cutting tip to sever a soft tissue attachment that is connected to the first end portion and the second bone.

8. The method of claim 6, wherein the soft tissue comprises a plantar tarsometatarsal ligament, and the joint is a TMT joint.

9. The method of claim 1, wherein the step of driving the insertion member comprises causing a cutting tip of the insertion member to completely separate the first end portion from the remaining portion of the first bone, such that the first end portion defines a first bone sliver.

10. The method of claim 1, wherein the first end portion is completely separated from the remaining portion of the first bone, such that the first end portion defines a first bone sliver.

11. The method of claim 1, wherein the step of driving the insertion member comprises driving an extension of the insertion member through a channel of a housing that also receives the paddle member.

12. The method of claim 11, wherein the step of driving the insertion member comprises engaging a handle with a thumb, grasping the housing member with one or more fingers, and driving the handle in the insertion direction so as to drive the extension in the insertion direction, wherein the extension extends from the handle.

13. The method of claim 1, further comprising the steps of driving at least one K-wire into the first bone, driving at least one K-wire into the second bone, and inserting a correction guide over the K-wires after cutting the first and second bones, thereby repositioning the first bone with respect to the second bone.

14. The method of claim 13, wherein the first bone is a metatarsal bone, the second bone is a cuneiform, and the joint is a TMT joint.

15. A bone removal tool comprising:
a housing including an upper end, a lower end opposite the upper end in a downward direction, and a channel extending from the upper end to the lower end;
a paddle member extending from the lower end of the housing, the paddle member including a paddle shaft and a paddle head; and
an insertion member translatably received within the channel, such that the insertion member is translatable in the downward direction with respect to the paddle member from a retracted position to an advanced position.

16. The bone removal tool of claim 15, wherein the paddle head defines a surface that faces the insertion member when the insertion member is in the advanced position, and the head comprises a plurality of retention features that extend from the surface toward the insertion member.

17. The bone removal tool of claim 16, wherein the retention features extend in an upward direction opposite the downward direction as they extend away from the surface of the paddle head.

18. The bone removal tool of claim 15, wherein the insertion member comprises a handle and an extension that extends from the handle, wherein the insertion member is translatable in the downward direction until the handle is received by a concave surface of the housing.

19. The bone removal tool of claim 15, wherein the extension is oriented substantially parallel with the paddle shaft.

20. The bone removal tool of claim 15, wherein the insertion member includes a cutting tip that is offset from the paddle head in the downward direction when the insertion member is in the advanced position.

\* \* \* \* \*